United States Patent
Nambu et al.

(10) Patent No.: US 9,494,565 B2
(45) Date of Patent: Nov. 15, 2016

(54) HATCHING EGG INSPECTION APPARATUS WITH VIBRATION ISOLATION

(71) Applicant: NABEL Co., Ltd., Kyoto-shi, Kyoto (JP)

(72) Inventors: Kunio Nambu, Kyoto (JP); Kenji Yasuda, Kyoto (JP); Toyoaki Ohashi, Kyoto (JP); Hiroshige Iguchi, Kyoto (JP)

(73) Assignee: NABEL Co., Ltd., Kyoto-shi, Kyoto (JP)

( * ) Notice: Subject to any disclaimer, the term of this patent is extended or adjusted under 35 U.S.C. 154(b) by 0 days.

(21) Appl. No.: 15/156,348

(22) Filed: May 17, 2016

(65) Prior Publication Data

US 2016/0255820 A1    Sep. 8, 2016

Related U.S. Application Data

(63) Continuation of application No. 14/399,160, filed as application No. PCT/JP2014/063019 on May 16, 2014, now Pat. No. 9,435,783.

(30) Foreign Application Priority Data

Jun. 14, 2013  (JP) ................................. 2013-125303
Jul. 1, 2013   (JP) ................................. 2013-138455
Jul. 29, 2013  (JP) ................................. 2013-156765

(51) Int. Cl.
  *G01N 33/08*    (2006.01)
  *A01K 43/00*    (2006.01)
  (Continued)

(52) U.S. Cl.
  CPC .............. *G01N 33/085* (2013.01); *A01K 43/00* (2013.01); *G01N 21/49* (2013.01); *G01N 21/8806* (2013.01); *G01N 33/08* (2013.01); *G01N 2021/845* (2013.01)

(58) Field of Classification Search
  CPC ............... G01N 33/08; G01N 33/085; G01N 21/8806; G01N 21/49; G01N 2021/845; G01N 35/02; G01N 35/04
  See application file for complete search history.

(56) References Cited

U.S. PATENT DOCUMENTS 2,736,456 A   2/1956   Clifford et al.
4,671,652 A   6/1987   van Asselt et al.
(Continued)

FOREIGN PATENT DOCUMENTS

CN   101123875   *   9/2005   ........... A01K 45/007
CN   201732068   *   5/2010   ............. G01N 21/90
(Continued)

OTHER PUBLICATIONS

Chinese Office Action No. 201480001098.0.*
(Continued)

*Primary Examiner* — Michael P LaPage
(74) *Attorney, Agent, or Firm* — Shinjyu Global IP

(57) ABSTRACT

A hatching egg inspection apparatus includes: a plurality of light emitter, the light emitter being disposed two dimensionally at prescribed positions; light receiver, which are provided in a one-to-one relationship with the light emitter and each of which receives light from the corresponding light emitter; and an egg container, which is for arraying in advance a hatching egg between each of the light emitter and the light receiver corresponding thereto. Each hatching egg is inspected by the corresponding light receiver that receives, among the lights from all the light emitter, transmitted light that transmitted through the interior of the hatching egg. When one light emitter of the plurality of light emitter is emitting light, other of the light emitter within a prescribed range centered on the one light emitter do not emit light.

7 Claims, 15 Drawing Sheets

(51) Int. Cl.
 *G01N 21/49* (2006.01)
 *G01N 21/88* (2006.01)
 *G01N 21/84* (2006.01)

(56) References Cited

U.S. PATENT DOCUMENTS

| | | | | |
|---|---|---|---|---|
| 5,900,929 | A | * | 5/1999 | Hebrank ............... G01N 33/085 356/52 |
| 2002/0157613 | A1 | * | 10/2002 | Phelps ................... A01K 45/00 119/6.8 |
| 2003/0156273 | A1 | | 8/2003 | Kageyama et al. |
| 2004/0065263 | A1 | * | 4/2004 | Hebrank ................ A01K 43/00 119/6.8 |
| 2006/0082759 | A1 | * | 4/2006 | Hebrank ................ G01N 33/08 356/53 |
| 2009/0201323 | A1 | | 8/2009 | Robert et al. |
| 2010/0026989 | A1 | * | 2/2010 | Wildenbeest ........ G01N 33/085 356/53 |
| 2010/0141933 | A1 | | 6/2010 | Nadreau et al. |
| 2011/0067633 | A1 | * | 3/2011 | Correa ................. A01K 45/007 119/6.8 |
| 2012/0318981 | A1 | | 12/2012 | Steiner et al. |

FOREIGN PATENT DOCUMENTS

| | | |
|---|---|---|
| JP | 06-011679 A | 1/1994 |
| JP | 2003-329578 A | 11/2003 |
| JP | 2011-106892 A | 6/2011 |
| JP | 2011-191460 A | 9/2011 |

OTHER PUBLICATIONS

International Search Report of Int'l Appln. No. PCT/JP2014/063019 issued on Jun. 24, 2014.

* cited by examiner

| a1 (1) | a2 (8) | a3 (15) | h1 (22) | h2 (29) | h3 (36) |
|---|---|---|---|---|---|
| b1 (2) | b2 (9) | b3 (16) | i1 (23) | i2 (30) | i3 (37) |
| c1 (3) | c2 (10) | c3 (17) | j1 (24) | j2 (31) | j3 (38) |
| d1 (4) | d2 (11) | d3 (18) | k1 (25) | k2 (32) | k3 (39) |
| e1 (5) | e2 (12) | e3 (19) | l1 (26) | l2 (33) | l3 (40) |
| f1 (6) | f2 (13) | f3 (20) | m1 (27) | m2 (34) | m3 (41) |
| g1 (7) | g2 (14) | g3 (21) | n1 (28) | n2 (35) | n3 (42) |

FIG. 7

| a1 (1) | a2 (8) | a3 (15) | h1 (1) | h2 (8) | h3 (15) |
|---|---|---|---|---|---|
| b1 (2) | b2 (9) | b3 (16) | i1 (2) | i2 (9) | i3 (16) |
| c1 (3) | c2 (10) | c3 (17) | j1 (3) | j2 (10) | j3 (17) |
| d1 (4) | d2 (11) | d3 (18) | k1 (4) | k2 (11) | k3 (18) |
| e1 (5) | e2 (12) | e3 (19) | l1 (5) | l2 (12) | l3 (19) |
| f1 (6) | f2 (13) | f3 (20) | m1 (6) | m2 (13) | m3 (20) |
| g1 (7) | g2 (14) | g3 (21) | n1 (7) | n2 (14) | n3 (21) |

FIG. 8

| a1 (1) | a2 (4) | a3 (7) | h1 (1) | h2 (4) | h3 (7) |
| b1 (2) | b2 (5) | b3 (8) | i1 (2) | i2 (5) | i3 (8) |
| c1 (3) | c2 (6) | c3 (9) | j1 (3) | j2 (6) | j3 (9) |
| d1 (1) | d2 (4) | d3 (7) | k1 (1) | k2 (4) | k3 (7) |
| e1 (2) | e2 (5) | e3 (8) | l1 (2) | l2 (5) | l3 (8) |
| f1 (3) | f2 (6) | f3 (9) | m1 (3) | m2 (6) | m3 (9) |
| g1 (10) | g2 (11) | g3 (12) | n1 (10) | n2 (11) | n3 (12) |

FIG. 9

HATCHING EGG INSPECTION APPARATUS WITH VIBRATION ISOLATION

CROSS-REFERENCE TO RELATED APPLICATIONS

This application is a continuation application of and claims priority to U.S. application Ser. No. 14/399,160 filed on Nov. 6, 2014, which claims priority to International Application PCT/JP2014/063019, with an international filing date of May 16, 2014 which claims priority to Japanese Patent Application No. JP2013-125303 filed on Jun. 14, 2013, Japanese Patent Application No. JP2013-138455 filed on Jul. 1, 2013, and Japanese Patent Application No. JP2013-156765 filed on Jul. 29, 2013. The entire disclosures of U.S. application Ser. No. 14/399,160, International Application PCT/JP2014/063019, Japanese Patent Application No. JP2013-125303, Japanese Patent Application No. JP2013-138455, and Japanese Patent Application No. JP2013-156765 are hereby incorporated herein by reference.

TECHNICAL FIELD

The present invention relates to a hatching egg inspection apparatus and a hatching egg inspecting method that determine the viability of hatching eggs, and more particularly relates to a hatching egg inspection apparatus and a hatching egg inspecting method that perform a viability determination based on information related to biological activity such as vital signs.

BACKGROUND

Eggs as represented by chicken eggs and the like include, in addition to eggs for eating, eggs for producing chicks, eggs for manufacturing vaccines, and the like. Such eggs are called "hatching eggs" in particular. Hatching eggs are placed in an apparatus that provides a prescribed environment, such as a constant temperature, as in an incubator, and are then incubated. In an incubator, hatching eggs are loaded onto a dedicated tray, which is called a setter tray, after which the incubating process is started.

In the incubating process, the day upon which the process is started is referred to as the incubation start day, and the number of days that have elapsed since the incubation start day is referred to as the incubation day count. Chicks are born on approximately the 21st day of incubation. On the 18th or 19th day of incubation, in preparation for the hatching of the hatching eggs, a procedure is performed wherein the hatching eggs are transferred from the setter tray to a dedicated tray called a hatcher tray. At the time of this transfer procedure, a prescribed inspection, such as a viability determination, is performed. In addition, with regard to hatching eggs for the manufacture of vaccines, a prescribed inspection, such as a viability determination, is performed on the hatching eggs on the 10th day of incubation immediately prior to the injection of a virus.

Incidentally, in the hatching process, not all the hatching eggs develop normally; for example, a certain percentage of eggs are unfertilized from the start; in addition, there are developmentally stopped eggs, which are eggs wherein the development of the embryos has adversely stopped during the incubating process. The contents of such unfertilized eggs, developmentally stopped eggs, and the like have adversely rotted, and such eggs are called rotten eggs.

Usually, hatching eggs for the production of chicks are inoculated with a vaccine in the hatching egg state in order to reduce their risk of becoming infected with a contagious disease and the like after hatching; however, when hatching eggs housed in the setter tray are inoculated with a vaccine, there are cases wherein those hatching eggs whose internal pressure has risen due to rotting adversely explode because of the shock that occurs when a hypodermic needle makes contact with the shell. In addition, although such hatching eggs may not explode, the hypodermic needle may adversely become contaminated owing to the inoculation of rotten eggs with the vaccine, and thereby other healthy hatching eggs may also be adversely contaminated by that contaminated hypodermic needle. Furthermore, if a hatching egg explodes after being transferred to the hatcher tray, hatched chicks may adversely become contaminated.

To prevent such explosions and contamination, an inspection is performed that separates the hatching eggs into "viable eggs," which are hatching eggs whose embryos are viable, and "inviable eggs," which are, for example, unfertilized eggs or developmentally stopped eggs wherein the embryos have died. Namely, a hatching egg viability determination is performed. Conventionally, optical techniques are principally employed in a hatching egg viability determination. In one of these techniques, the viability determination is performed by radiating a hatching egg with prescribed light and then analyzing time varying components of the light that transmits through the hatching egg. In so doing, hatching eggs that have been determined to be inviable eggs are promptly eliminated, which prevents viable eggs from becoming contaminated.

The time varying components of the light that transmits through a viable egg include information related to biological activity called vital signs, such as the motility of the embryo, the heart rate of the embryo, and the like; however, the time varying components of the light that transmits through a developmentally stopped egg, wherein the embryo has died, do not contain vital signs. Accordingly, Patent Document 1 (Japanese Unexamined Patent Application Publication No. 2011-106892) proposes an apparatus that determines the viability of a hatching egg based on the presence of these vital signs.

SUMMARY

Nevertheless, because vital signs are detected based on extremely subtle fluctuations in the motility, the heart rate, and the like of an embryo during development, it is not easy to make an accurate viability determination based on vital signs, and there are numerous cases wherein a mistaken determination occurs. The mistaken determination of the viability of a hatching egg greatly affects the production of chicks, the manufacture of vaccines, and the like. Accordingly, there is a demand for a hatching egg inspection apparatus wherein mistaken determinations seldom occur.

The present invention was developed in accordance with the abovementioned demand, and an object of the present invention is to reduce the incidence of mistaken determinations in hatching egg inspection.

A hatching egg inspection apparatus according to an aspect of the present invention includes: a plurality of light emitter, the light emitter being disposed two dimensionally at prescribed positions; light receivers, which are provided in a one-to-one relationship with the light emitters and each of which receives light from the corresponding light emitter; and an egg container, which is for arraying in advance a hatching egg between each of the light emitter and the light receiver corresponding thereto. Each hatching egg is inspected by the corresponding light receiver that receives, among the lights from all the light emitters, transmitted light that transmitted through the interior of the hatching egg. Of the plurality of light emitters, when one of the light emitters is emitting light, other of the light emitters within a prescribed range centered on the one light emitters do not emit light.

The present invention can reduce the incidence of mistaken determinations in hatching egg inspection.

BRIEF DESCRIPTION OF DRAWINGS

FIG. 7 is a conceptual diagram for explaining a first light ON pattern of a plurality of light emitter of the inspection apparatus according to the embodiment of the present invention.

FIG. 8 is a conceptual diagram for explaining a second light ON pattern of the plurality of the light emitter of the inspection apparatus according to the embodiment of the present invention.

FIG. 9 is a conceptual diagram for explaining a third light ON pattern of the plurality of the light emitter of the inspection apparatus according to the embodiment of the present invention.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

A hatching egg inspection apparatus and a hatching egg inspecting method according to an embodiment of the present invention will now be explained. The following explains preferred embodiments of the inspection apparatus and the inspecting method, which inspect hatching eggs used in the production of chicken chicks, the manufacture of vaccines, and the like, referencing the drawings. However, the hatching egg inspection apparatus and the hatching egg inspecting method according to the present invention can also be used to inspect the hatching eggs of other than those of chicken chicks.

<Hatching Eggs>

The hatching egg of a chicken generally hatches approximately 21 days after the egg is laid. During that interval, such a hatching egg is called an incubating egg, and an embryo develops, in accordance with its age in days, inside the hatching egg. In the explanation of the present embodiment, the embryo on, for example, the 10th day after being laid, namely, the embryo inside a 10 day old hatching egg, is called a 10th day embryo.

Hatching eggs are used in the manufacture of vaccines in addition to the production of chicks. In the case of such hatching eggs for the manufacture of vaccines, the 11th day embryo or the 12th day embryo is inoculated with a virus and, after warming the hatching egg for 2-3 days, the culture solution that contains the cultured virus is recovered. The optical transmissiveness of a hatching egg generally degrades as the egg ages and the embryo develops.

<Hatching Egg Inspection Apparatus>

Figure 1:
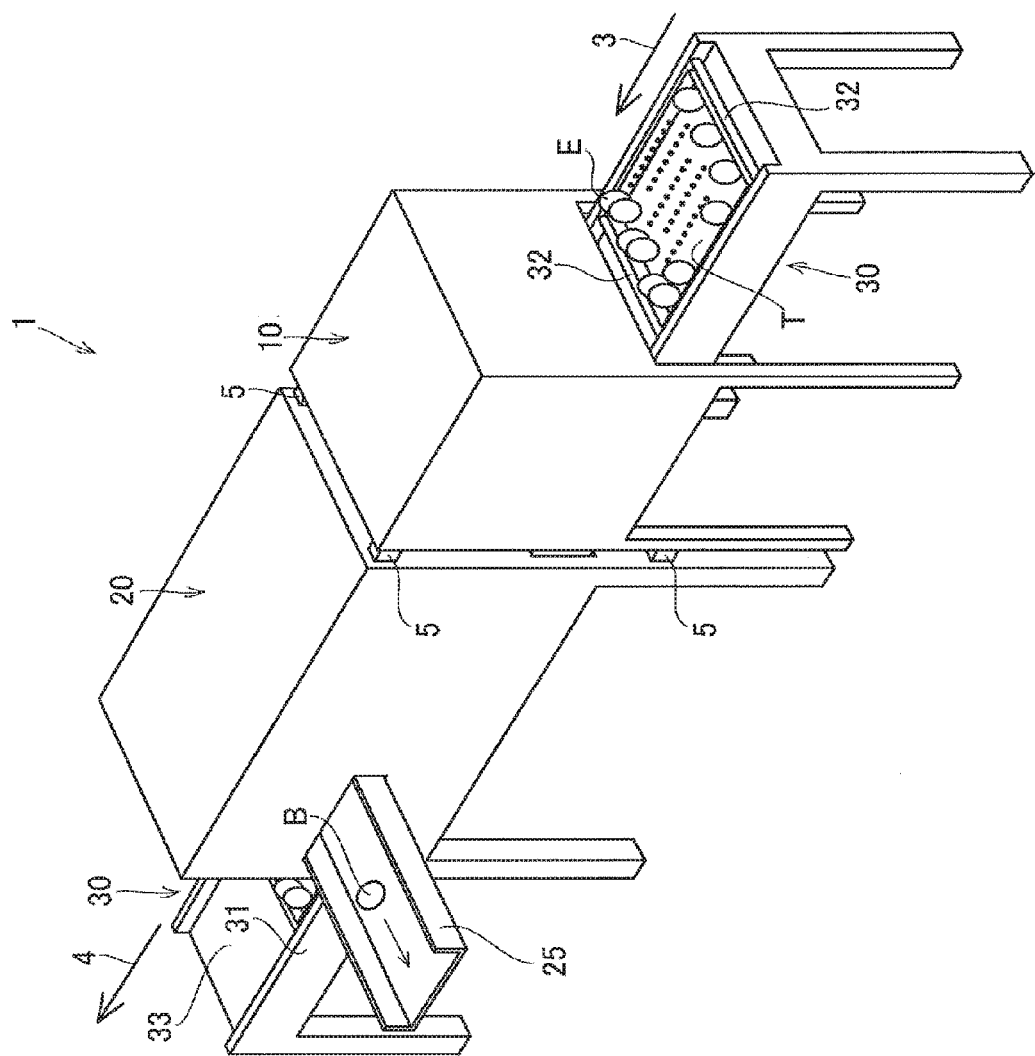
FIG. 1 is an oblique view that shows a hatching egg inspection apparatus according to an embodiment of the present invention.
Figure 2:
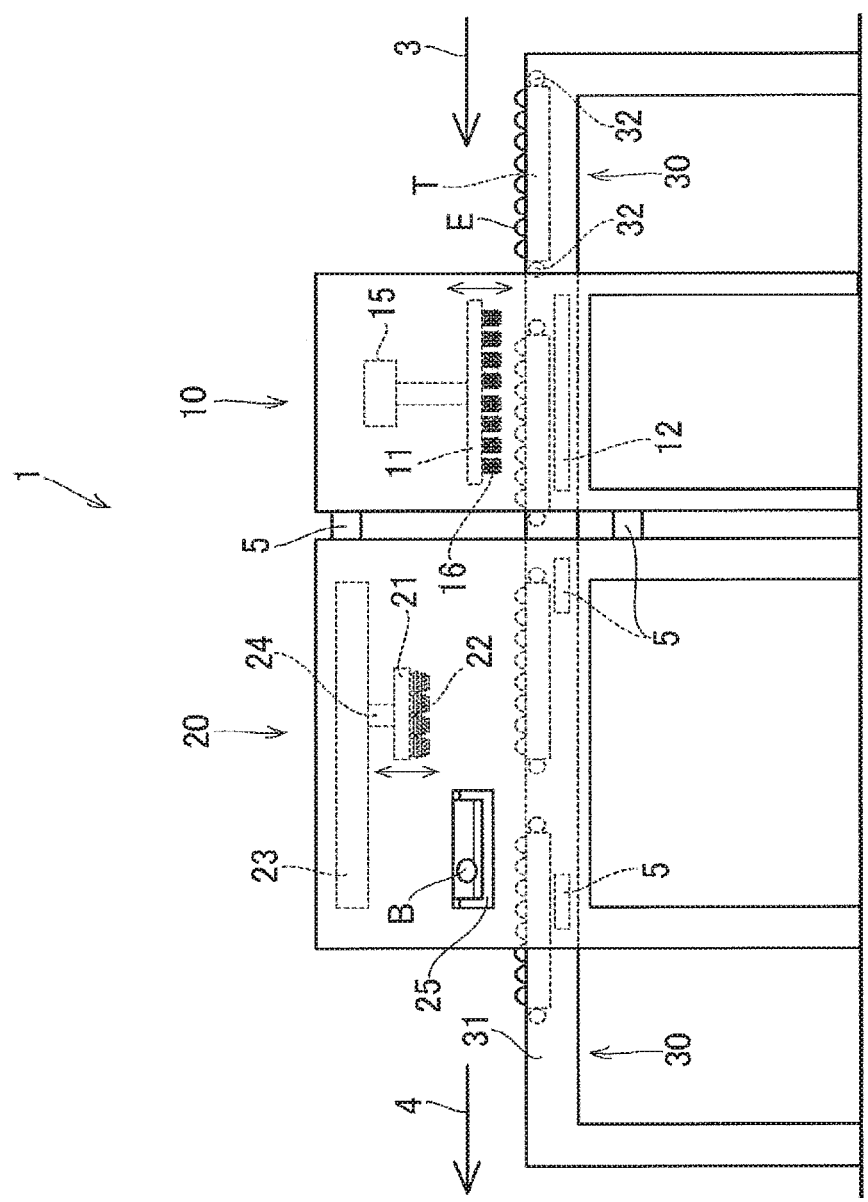
FIG. 2 is a front view of the hatching egg inspection apparatus shown in FIG. 1.

A hatching egg inspection apparatus 1 according to an embodiment of the present invention will now be explained. As shown in FIG. 1 and FIG. 2, the hatching egg inspection apparatus 1 includes: an inspecting part 10, which inspects, for example, the viability of hatching eggs E based on vital signs; a transfer part 20, which transfers the hatching eggs E based on inspection results of the inspecting part 10; and conveying parts 30 that convey an egg container T, which houses a plurality of the hatching eggs E, such that the egg container T passes through the inspecting part 10 and the transfer part 20.

Figure 3:
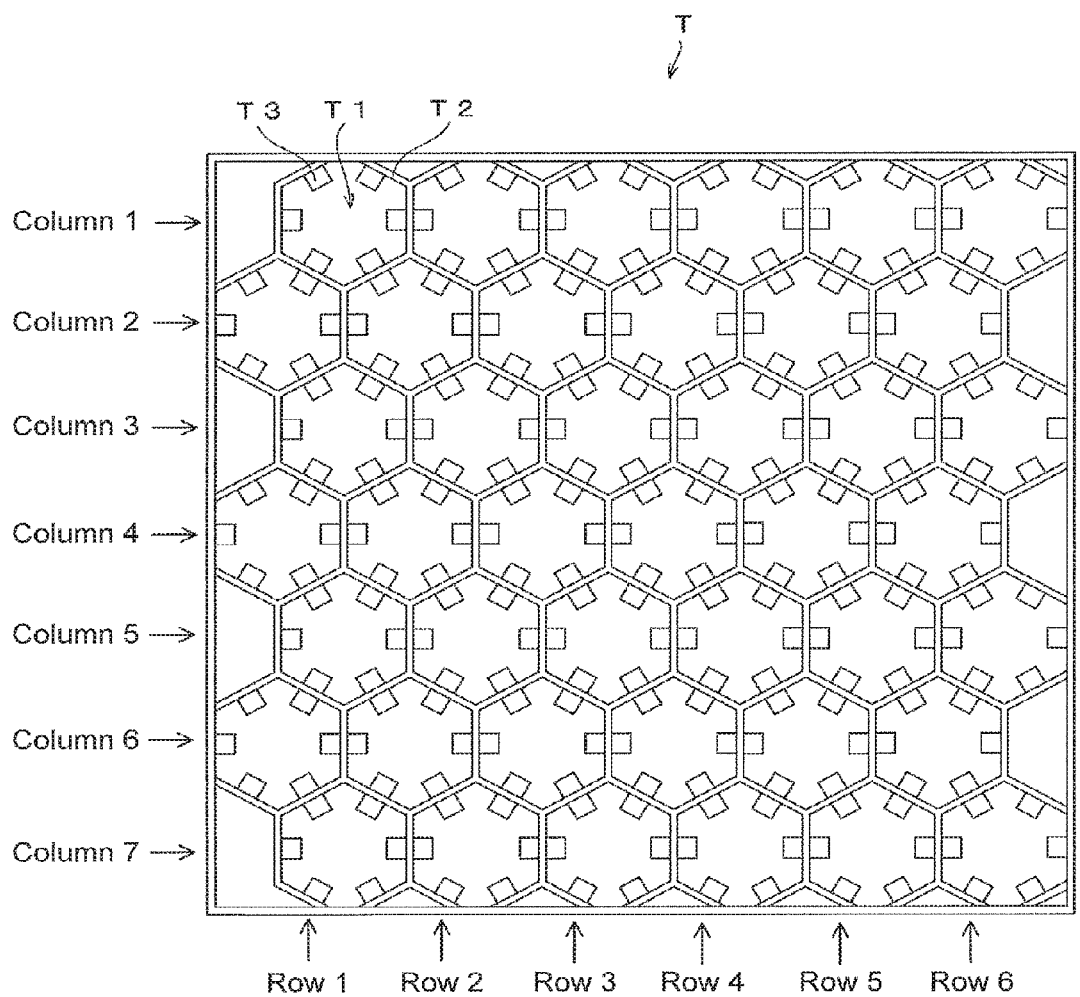
FIG. 3 is a plan view that shows an egg container that is used in the hatching egg inspection apparatus shown in FIG. 1.

As shown in FIG. 3, the egg container T conveyed by the conveying parts 30 is generally called a setter tray and includes a plurality of egg seats T1, which is provided two dimensionally in m rows×n columns (wherein m and n are natural numbers). In the egg container T according to the present embodiment, the egg seats T1 in each row are offset from one another, and the plurality of the egg seats T1 is provided in 6 rows×7 columns. The hatching eggs E are housed in the egg container T in 6 rows×7 columns, each egg seat T1 being filled with one hatching egg E in the state wherein the pointed end of the hatching egg E faces downward and the blunt end of the hatching egg E faces upward.

In each egg seat T1, a plurality of projecting parts T3, which is for supporting the hatching egg E from below, is formed in a frame part T2, which conforms to the shape of the hatching egg and is for supporting the hatching egg from the side; thereby the hatching egg E is held from the side and from below. Light from below is caused to pass through a portion of each egg seat T1 other than the frame part T2 and the projecting parts T3.

In addition to the one shown in FIG. 3, there are egg containers wherein the egg seats are provided in a grid without being offset. In addition, in the present embodiment, the hatching egg E is housed in a state wherein the pointed end faces downward; however, the egg seats T1 may be filled with hatching eggs that face any direction as long as the hatching eggs can be inspected. In addition, the egg container T may be some other container or the like as long as the container can be inspected by the hatching egg inspection apparatus 1.

Figure 4:
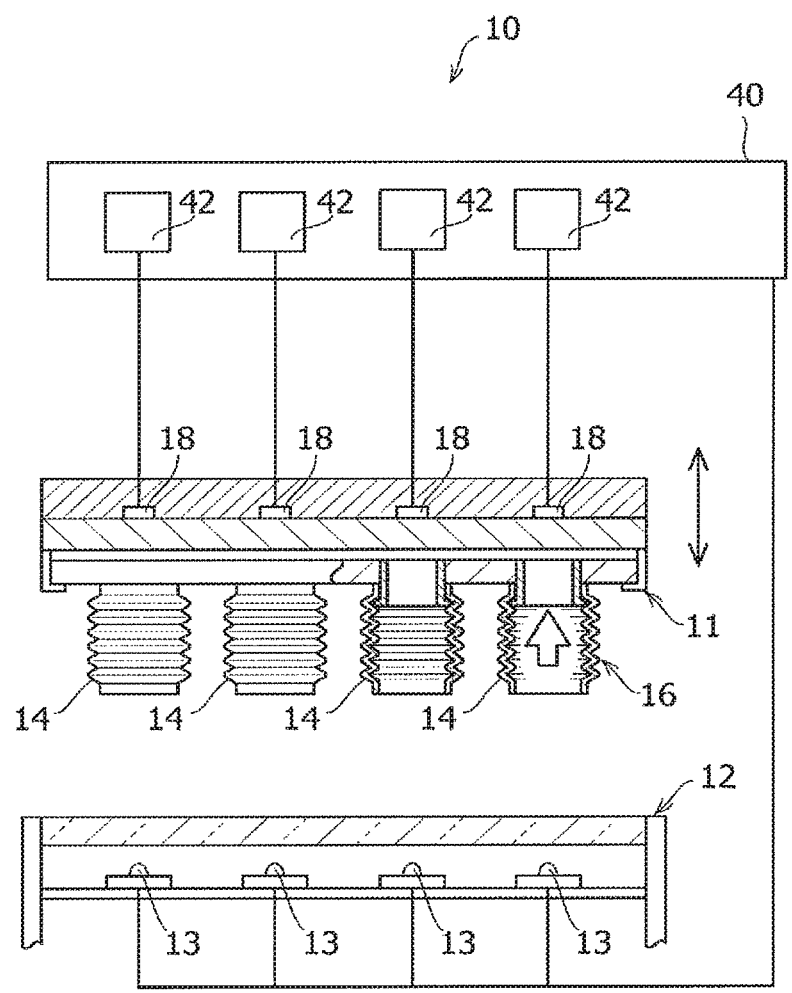
FIG. 4 is a front view that shows the configuration of an inspecting part of the hatching egg inspection apparatus shown in FIG. 1.
Figure 5:
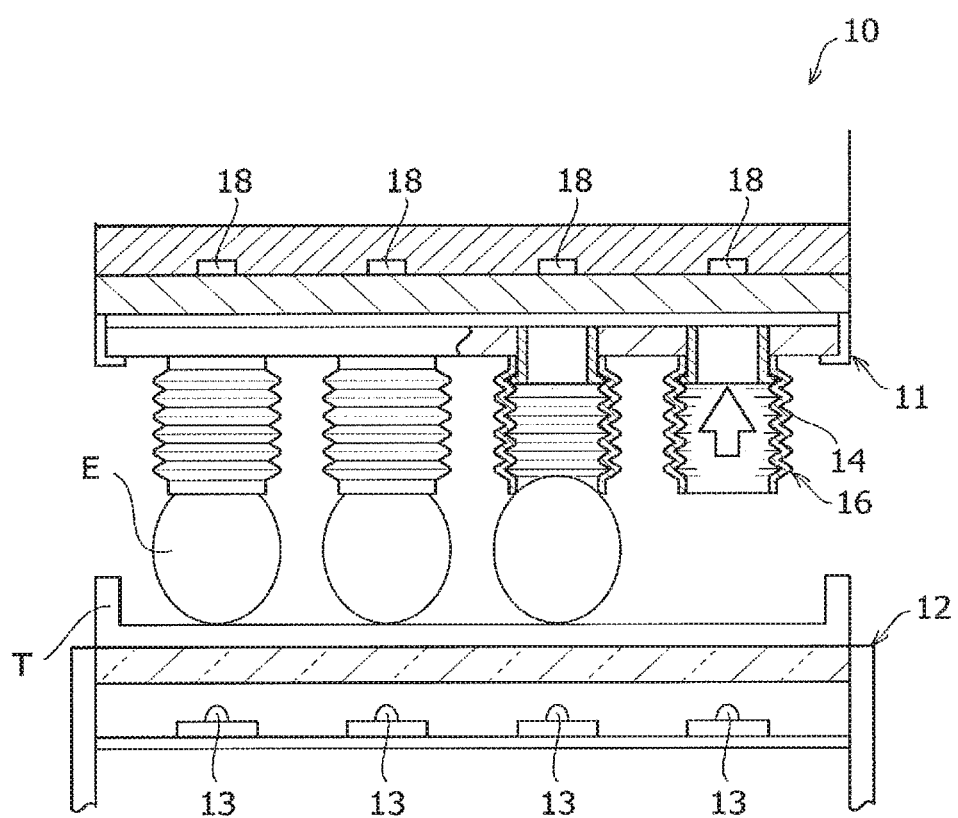
FIG. 5 is a front view that shows a state wherein eggs are disposed in the inspecting part shown in FIG. 4.

Referencing FIG. 2 once again, the inspecting part 10 is fixed to the floor surface. As shown in FIG. 2, FIG. 4, and FIG. 5, the inspecting part 10 includes: a light emitting part 12, which radiates prescribed light toward the hatching eggs E from below; and a measuring device 11, which measures the light that is radiated from the light emitting part 12 and that transmits through the hatching eggs E. The light emitting part 12 includes a plurality of light emitter 13 that corresponds to the hatching eggs E housed in the egg container T and is arranged two dimensionally. Each of the light emitter 13 includes a light emitting device, such as a light emitting diode, and radiates light upward. The light emitting device may be, for example, a laser device or the like as long as it is a device that emits light in a prescribed wavelength region.

The measuring device 11 includes: numerous light passing device 16, each of which is for the purpose of passing therethrough only the light that has transmitted through its corresponding hatching egg E and includes a cap 14 that contracts when it contacts its corresponding hatching egg E; light receiver 18, which receive the light that passes through the light passing device 16; and a control unit 40, which controls the hatching egg inspection apparatus 1. Each of the light receiver 18 includes a light receiving device such as a photodiode. The light receiver is not limited to a photodiode or the like as long as it can capture, as a signal, the prescribed light that transmits through the hatching egg E.

One light emitter 13 and its corresponding light passing device 16 and light receiver 18 are provided in a one-to-one relationship and constitute one inspection unit. One inspection unit is provided in correspondence with one hatching egg placed at a prescribed inspection position. In the present embodiment, 42 inspection units are provided, two dimensionally in 6 rows×7 columns, corresponding to 42 hatching eggs arrayed in 6 rows×7 columns. In the example shown in FIG. 4 and FIG. 5, only four inspection units are shown in order to simplify the explanation.

The openings of the caps 14 are brought into contact with the hatching eggs E in the state wherein the egg container T, in which the hatching eggs E are housed, has been carried into the inspecting part 10 by the conveying part 30, which is described below. The caps 14 can expand and contract and tightly contact the hatching eggs E. In this state, each cap 14 shields the light that passes through its interior from other light. Accordingly, each light receiver 18 can only receive the light, of the light radiated from the light emitter 13, which passes through its corresponding cap 14.

However, one hatching egg E transmits therethrough, in addition to the light from the corresponding one light emitter 13 that is provided, the light from other light emitter 13 (e.g., from adjacent light emitter 13). Thereby, there are cases in which the one light receiver 18 that corresponds to one hatching egg and one light emitter 13 adversely receives also light from another light emitter 13 via the corresponding one cap 14.

Because one light receiver 18 inspects a hatching egg based on the light from one light emitter 13, if the one light receiver 18 receives light from another light emitter 13, it may hinder accurate inspection. In particular, the transmissiveness of a hatching egg whose embryonic development is not advanced, as in a 10th day embryo, is high, which consequently greatly affects the one light receiver 18.

Figure 6:
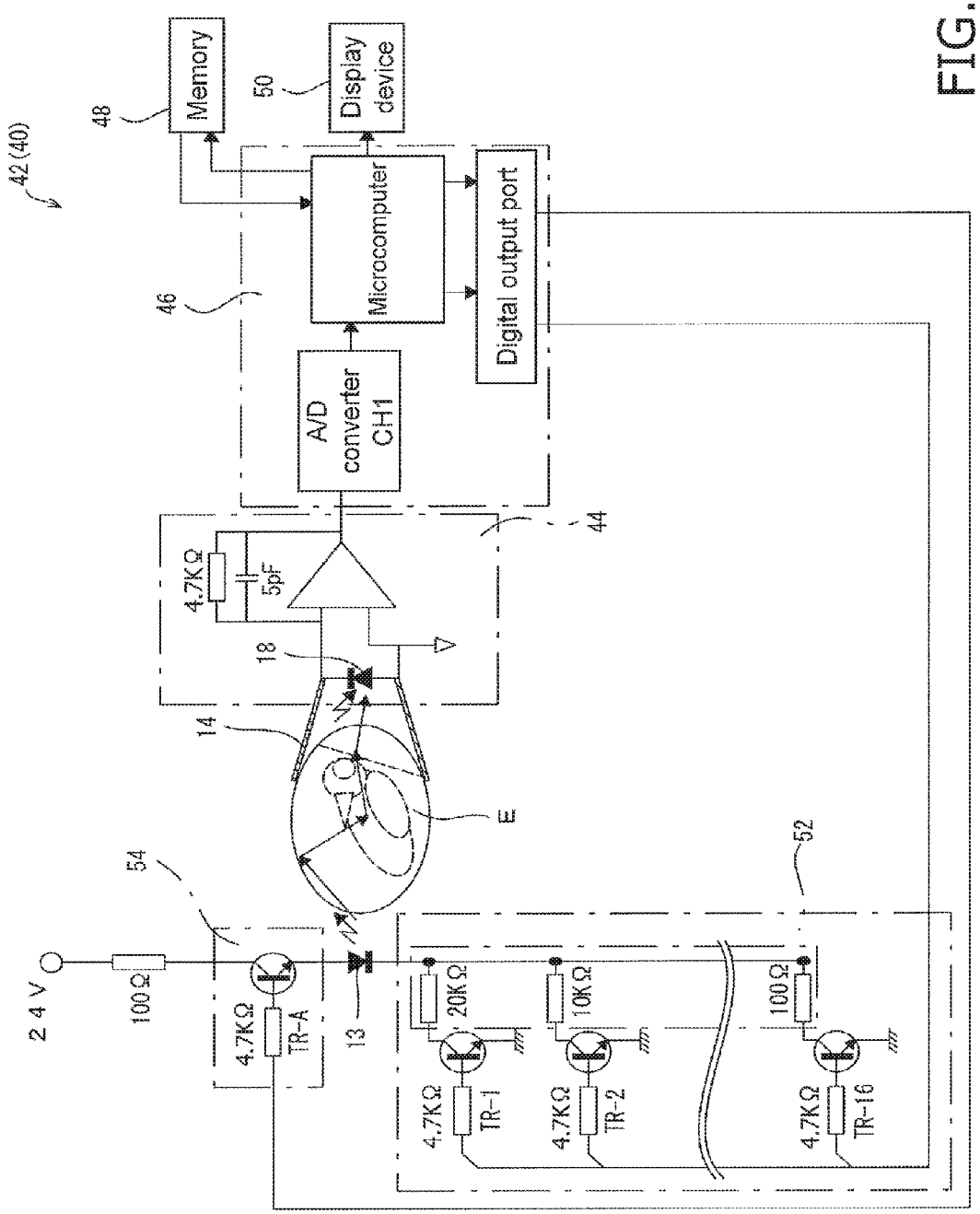
FIG. 6 is a block diagram that shows an inspection control apparatus of a control unit shown in FIG. 4.

The control unit 40 includes a plurality of inspection control devices 42, which is provided in a one-to-one relationship with the hatching eggs E to be inspected, namely, with the plurality of inspection units. As shown in FIG. 6, the inspection control device 42 includes at least a photoelectric converting unit 44, a determination calculating unit 46, a storage unit 48 (memory), a display unit 50 (display device), a luminous energy control unit 52, and a light ON/OFF switch 54, as in the hatching egg inspection apparatus of Japanese Unexamined Patent Application Publication No. 2011-106892.

The luminous energy control unit 52 and the light ON/OFF switch 54 are connected with the light emitter 13 and control the ON/OFF state, the luminous energy, and the like of the light emitter 13. Accordingly, in the state wherein the hatching eggs E are arrayed at their prescribed inspection positions, in each inspection control device 42, the light ON/OFF switch 54 can turn ON the light emitter 13 (i.e., cause the light emitter 13 to emit light), the luminous energy control unit 52 can adjust the luminous energy by controlling the light emitter 13 and, after the inspection ends, the light ON/OFF switch 54 can turn OFF the light emitter 13.

The light ON/OFF switch 54 can periodically cause the light emitter 13 to emit light multiple times by periodically switching multiple times. Accordingly, under the control of the luminous energy control unit 52 and the light ON/OFF switch 54, the light emitter 13 can be caused to emit light such that it has a rectangular waveform of a desired period and intensity. In addition, the luminous energy control unit 52 can cause the light emitter 13 to emit light with a desired waveform (e.g., a triangular waveform, a sine waveform, or the like) using an electronic circuit that is well known in the art.

Each photoelectric converting unit 44 is connected to its corresponding light receiver 18 and converts the light received by its light receiver 18 to an electrical signal. The determination calculating unit 46 includes a calculating apparatus, such as a microcomputer, is connected to the photoelectric converting unit 44, and inspects the activity of the hatching egg by analyzing the photoelectrically converted electrical signal.

The hatching egg activity includes information such as whether the embryo inside the hatching egg is viable or dead and, if viable, to what extent it is active (e.g., information about whether the embryo is not dead but dying). Accordingly, based on the activity, the viability of the hatching egg may be inspected and it is also possible to determine the degree of activity of the hatching egg.

The determination of this activity is performed, as recited in Japanese Unexamined Patent Application Publication No. 2011-106892 and Japanese Unexamined Patent Application Publication No. H09-127096, based on time varying biological information related to biological activity such as the heart rate, the fetal movement, and the like of the embryo inside the hatching egg E. Furthermore, as recited in Japanese Unexamined Patent Application Publication No. H09-127096, the heart rate and the fetal movement can be detected if the age in days is at least 8. In addition, if the determination calculating unit 46 cannot clearly determine the activity via inspection, then the determination calculating unit 46 can also make a determination that the activity is unknown.

In addition, the determination calculating unit 46 is connected to and controls the luminous energy control unit 52. The storage unit 48 is connected to the determination calculating unit 46 and stores, as appropriate, information for making the determination. The display unit 50 is connected to the determination calculating unit 46 and displays the determination result and the like.

The determination calculating unit 46 can inspect the viability of the hatching egg based also on the luminous energy that transmits through the hatching egg, which serves as information about the embryo inside the hatching egg; namely, based on information about the transmissiveness of the hatching egg E. For example, the hatching egg E whose transmitted luminous energy is markedly large can be determined to be an unfertilized egg, wherein an embryo has not formed, namely, it can be determined to be dead in the viability inspection (refer to Published Japanese Translation No. 2001-509895 of the PCT International Publication).

The light radiated from the light emitter 13 transmits through the hatching egg E and consequently possesses information related to the biological activity inside the hatching egg E. The information related to the biological activity includes information, such as heart rate and fetal movement, that changes slightly over short periods of time. The photoelectric converting unit 44 converts the light received by the light receiver 18 into an electrical signal. Accordingly, the determination calculating unit 46 can acquire information related to the biological activity by analyzing slight fluctuations in the electrical signal.

As in the inspection apparatus recited in Japanese Unexamined Patent Application Publication No. 2011-10689, the luminous energy control unit 52 controls the light emitter 13 in accordance with the luminous energy received by the corresponding light receiver 18, namely, in accordance with the luminous energy that transmits through the corresponding hatching egg E, such that the luminous energy of the light source is suited to the corresponding hatching egg. However, a configuration may be adopted wherein, when the luminous energy is not controlled, all the light emitter 13 emit light with the same luminous energy.

Next, the control details of the control unit 40 will be explained. The control unit 40 provides supervisory control of the plurality of inspection control devices 42, and each inspection control device 42 controls one inspection unit so as to inspect one hatching egg. Accordingly, the hatching egg inspection apparatus 1 can independently control the light emitter 13 and the light receiver 18 corresponding to each hatching egg E.

The hatching egg inspection apparatus 1 inspects, as one inspection unit, the plurality of hatching eggs E housed in one egg container T. Namely, the plurality of hatching eggs E housed in the one egg container T is conveyed and inspected in units of the inspection unit. The egg container T is stopped inside the inspecting part 10 by the conveying parts 30 at the time of the inspection, and thereby the plurality of hatching eggs E is placed in a state wherein the hatching eggs E are arrayed at their prescribed inspection positions.

Prior to the inspection, the caps 14 of the corresponding light passing member 16 contact the hatching eggs E. Thereby, the state results wherein the hatching eggs E can be inspected (refer to FIG. 5). In this state, the one inspection control device 42 causes the light emitter 13 connected thereto to emit light. The light emitted from the light emitter 13 transmits through the hatching egg E and is received by the light receiver 18.

Synchronized to the emission of light by the light emitter 13, the light receiver 18 detects extremely slight changes in the light in order to measure the heart rate of the embryo. Compared to the case wherein the amount of transmitted light is measured as in the inspection apparatus recited in Japanese Unexamined Patent Application Publication No. 2001-509895, the change in the light for measuring the heart rate of the embryo is extremely small.

In the present embodiment, each inspection control device 42 periodically emits light multiple times for the inspection of one hatching egg E. This light emission is adjusted to the extent that the heart rate of the embryo can be acquired as effective information based on, for example, the Shannon-Someya sampling theorem, which is well known in the art (refer to Japanese Unexamined Patent Application Publication No. 2011-106892). In addition, prior to the periodic emission of light multiple times, each inspection control device 42 adjusts the luminous energy of its light emitter 13 such that the luminous energy received by the light receiver 18 in accordance with the luminous energy transmitted through the hatching egg is optimal. Namely, the luminous energy of the light emitter 13 with respect to a hatching egg whose transmittance is high becomes small, and the luminous energy of the light emitter 13 with respect to a hatching egg whose transmittance is low becomes large.

The hatching egg inspection apparatus 1 inspects each hatching egg by the periodic emission of light multiple times. Thereby, it is also possible, using an information processing device, to eliminate to a certain extent the effect of the light emitted by other light emitter 18 received by the one light receiver 18 corresponding to the one light emitter 13. However, one hatching egg may be inspected by the one-time emission of light that does not change periodically, namely, by the emission of light having a simple one-step rectangular wave.

Next, light ON patterns of the plurality of light emitter 13 will be explained, referencing FIG. 7 through FIG. 9. FIG. 7 through FIG. 9 conceptually show, in the present embodiment, the light emitter 13, which are disposed with an offset, corresponding to the egg container T, wherein the egg seats T1 are offset. Forty-two of the light emitter 13 are provided in 6 rows×7 columns corresponding to the egg container T including 42 egg seats T1 likewise in 6 rows×7 columns.

In FIG. 7 through FIG. 9, the assigned symbols a1-n3 are for identifying the light emitter 13, and the numerals enclosed by the parentheses below indicate the order in which the light is turned ON. For example, (1) is denoted below a1 and (2) is denoted below b1, and therefore a1 first emits light and then b1 emits light. If (1) were denoted below both a1 and h1, then a1 and h1 would emit light synchronously.

In addition, in the present embodiment, each inspection control device 42 can control its corresponding light emitter 13 and light receiver 18 so as to independently inspect the corresponding hatching egg. Accordingly, the hatching egg inspection apparatus 1 can cause the plurality of light emitter 13 to emit light in, for example, the three types of light ON patterns described next.

As a first light ON pattern, when one light emitter 13 is emitting light, the inspection control devices 42 control the light emitter 13 such that other light emitter 13 within a prescribed range centered on the one light emitter 13 do not emit light. Namely, when the one light emitter 13 is turned ON, the other light emitter 13 are turned OFF.

As shown in FIG. 7, in the first light ON pattern, the light emitter 13 sequentially emit light in the order of a1, b1, c1, . . . , l3, m3, n3. Accordingly, when a1 is emitting light, the light emitter 13 other than a1, namely, b1-n3, do not emit light. Likewise, when a2 is emitting light, the light emitter 13 other than a2 do not emit light. In the present light ON pattern, only one light emitter 13 emits light in the egg container T at one time, and consequently the prescribed range is substantially the outer edge of the egg container T.

When one light emitter 13 is emitting light, certain other light emitter 13 within the prescribed range are turned OFF, and thereby the light of the other light emitter 13 within the prescribed range does not affect the light receiver 18 corresponding to the one light emitter 13. Therefore, according to the inspection apparatus 1, the inspection of hatching eggs can be performed accurately. In particular, when slight changes, as those of vital signs, are to be detected, that detection is not affected by periodic changes in other light emitter, which greatly improves inspection accuracy.

In the present embodiment, each light emitter 13 periodically emits light multiple times. The one time emission of light in the abovementioned order a1-n3 serves as one cycle, and the 42 light emitter 13 periodically emit light for multiple cycles. Accordingly, the inspection of the plurality of hatching eggs E of one inspection unit ends substantially at the same time (i.e., a1 and n3 are shifted by one cycle). However, a configuration may be adopted wherein the emission of light multiple times by each light emitter 13 is taken as one cycle and, every time each light emitter finishes one cycle, the next light emitter emits light for one cycle. In so doing, the inspection is completed in 42 cycles.

As a second light ON pattern, each inspection control device 42 is controlled such that, when one light emitter 13 is emitting light, the other light emitter 13 within the prescribed range do not emit light, and a certain one of the other light emitter 13 outside the prescribed range does emit light. Namely, when the one light emitter 13 is turned ON, the other light emitter 13 within the prescribed range are turned OFF, and another light emitter 13 outside of the prescribed range is turned ON. In the second light ON pattern, two of the light emitter 13 emit light with overlapped timing.

As shown in FIG. 8, in the second light ON pattern, of the 42 light emitter 13, 21 of the light emitter 13 disposed substantially on the left half in the figure sequentially emit light in the order of a1, b1, c1, . . . , e3, f3, g3 and, synchronized thereto, 21 of the light emitter 13 disposed substantially on the right half of the figure emit light in the order of h1-n1, h2-n2, h3-n3. Namely, a1 and h1 synchronously emit light (turn ON) and, at that time, the other light emitter 13 do not emit light (turn OFF). Subsequently, likewise, light is sequentially emitted wherein b1 and i1 are synchronized, c1 and j are synchronized, . . . , f3 and m3 are synchronized, and g3 and n3 are synchronized.

In the present light ON pattern, the prescribed range includes the light emitter 13 that are spaced apart from the one light emitter 13 that serves as the center by two of the light emitter 13. For example, h1 is spaced apart from a1 by three and is outside of the prescribed range from the a1; consequently, the h1 emits light synchronously with the a1. Furthermore, "synchronized" refers to the simultaneous emission of light by a plurality of the light emitter with at least some timing and to making the phases of the light emission waveforms coincide with one another.

According to the present light ON pattern, when the one light emitter is emitting light, the other light emitter within the prescribed range turn OFF, and thereby the lights of other light emitter within the prescribed range do not affect the light receiver corresponding to the one light emitter. Furthermore, the light emitter outside the prescribed range do emit light synchronized with the one light emitter, and consequently two hatching eggs are inspected simultaneously, which shortens the inspection processing time. Furthermore, the other light emitter outside of the prescribed range are spaced apart from the one light emitter that serves as the center, and consequently the effect on the one light receiver corresponding to the one light emitter is small to an extent that it can be ignored in the inspection.

In the present embodiment, each light emitter 13 periodically emit light multiple times, and consequently twenty one of the light emitter 13 periodically emits light for multiple cycles wherein the one time emission of light in the order of the abovementioned a1-g3, and, synchronized thereto, h1-n3, serves as one cycle. Accordingly, the plurality of hatching eggs E of one inspection unit ends substantially at the same time (i.e., a1 and g3 are shifted by one cycle). However, a configuration may be adopted wherein the emission of light multiple times by each light emitter 13 serves as one cycle and, every time each light emitter finishes one cycle, the next light emitting mean emits light for one cycle. In so doing, the inspection is completed in 21 cycles.

As a third light ON pattern, the inspection control devices 42 are controlled such that, when the one light emitter 13 is emitting light, the other light emitter 13 within the prescribed range do not emit light and a plurality of the other light emitter 13 outside of the prescribed range do emit light. Namely, when the one light emitter 13 is turned ON, the other light emitter 13 within the prescribed range are turned OFF and a plurality of other light emitter 13 outside of the prescribed range is turned ON. In the third light ON pattern, a maximum of four of the light emitter emit light synchronously.

In the third light ON pattern, as shown in FIG. 9, of the 42 light emitter 13, nine of the light emitter disposed in substantially the left half and substantially the upper half of the drawing sequentially emit light in the order of a1, b1, c1, a2, b2, c2, a3, b3, c3; synchronized thereto, nine of the light emitter 13 disposed in substantially the left half and substantially the lower half of the drawing emit light in the order of d1, e1, f1, d2, e2, f2, d3, e3, f3, nine of the light emitter 13 disposed in substantially the right half and substantially the upper half of the drawing emit light in the order of h1, i1, j1, h2, i2, j2, h3, i3, j3, and nine of the light emitter 13 disposed in substantially the right half and substantially the lower half of the drawing emit light in the order of k1, l1, m1, k2, l2, m2, k3, l3, m3. After these light emissions, g1 and n1 emit light synchronously, g2 and n2 emit light synchronously, and g3 and n3 emit light synchronously, in that order.

In the present light ON pattern, the prescribed range includes the light emitter that are spaced apart from the one light emitter 13 that serves as the center by two light emitter. For example, h1, which is spaced apart from a1 by three in the right direction, d1, which is spaced apart from a1 by three in the downward direction, and k1, which is spaced apart from a1 by approximately three diagonally, that is, toward the right and in the downward direction, are outside of the prescribed range, and consequently emit light synchronously with a1. Furthermore, "synchronized" refers to the simultaneous emission of light by a plurality of the light emitter with at least some timing and to making the phases of the light emission waveforms coincide with one another.

According to the present light ON pattern, when the one light emitter is emitting light, the other light emitter within the prescribed range are turned OFF, and thereby the lights of the other light emitter within the prescribed range do not affect the light receiver corresponding to the one light emitter. Moreover, because the light emitter outside of the prescribed range emit light synchronized to the one light emitter, a maximum of four hatching eggs are inspected simultaneously, which greatly shortens the inspection processing time. Furthermore, because the other light emitter outside of the prescribed range are spaced apart from the one light emitter that serves as the center, the effect on the one light receiver corresponding to the one light emitter is small enough to be ignored in the inspection.

In the present embodiment, each light emitter 13 periodically emits light multiple times, and consequently the plurality of light emitter 13 periodically emit light for multiple cycles, wherein one cycle is defined as the one time emission of light by the abovementioned a1-c3 and, synchronized thereto, d1-f3, h1-j3, k1-m3, and subsequently the one time emission of light by g1-g3 and n1-n3 synchronously. Accordingly, the inspection of the plurality of hatching eggs E of one inspection unit ends substantially at the same time (i.e., a1 and n3 are shifted by one cycle). However, a configuration may be adopted wherein the emission of light multiple times by each light emitter 13 serves as one cycle and, every time each light emitter finishes one cycle, the next light emitting mean emits light for one cycle. In so doing, the inspection is completed in 12 cycles.

In the various light ON patterns, the prescribed ranges are not limited to the abovementioned details and are modified where appropriate based on the effect that other light emitter 13 have on the one light receiver 18 corresponding to the one light emitter 13 that serves as the center. For example, if the light receiver 18 corresponding to the one light emitter 13 is not affected by other light emitter 13 that are two light emitter 13 away, then a1 and c1, a3, which are two light emitter 13 away from a1, may emit light simultaneously. In this case, the prescribed range within which the light emitter 13 are turned OFF includes the other light emitter 13 that are spaced apart by one light emitter 13.

In addition, the prescribed range is modified where appropriate also by the arrangement of the receiving seats of the egg container T. For example, the prescribed ranges are naturally different for a setter tray wherein the egg seats are provided offset from one another and a setter tray wherein the egg seats are provided in a grid. In addition, the light ON pattern is also modified where appropriate in accordance with the modification of the prescribed range. Although various light ON patterns, light emission cycles, and the like were explained, these may be modified or combined where appropriate in accordance with the details and purpose of the inspection.

In correspondence with the light ON pattern of the light emitter 13 as described above, the light receiver 18 receive light that includes information about the hatching eggs E. The timing with which the light receiver 18 receive those lights can be selected as appropriate. The lights received by the light receiver 18 are converted to electrical signals, and the inspection control devices 42 analyze information about the interiors of the hatching eggs from those electrical signals.

In the present embodiment, the inspection units are provided such that they number the same as the plurality of hatching eggs E of one inspection unit. However, an inspection may be performed by configuring fewer inspection units than the plurality of hatching eggs E of one inspection unit, and adapting the inspection units to the plurality of hatching eggs E of a different number. For example, 42 hatching eggs may be inspected by making the 42 hatching eggs in 6 rows×7 columns serve as one inspection unit and configuring 21 inspection units in 3 rows×7 columns, wherein each inspection unit is adapted to two different hatching eggs. In addition, an inspection may be performed wherein the number of inspection units is greater than the number of hatching eggs E in one inspection unit. At this time, the plurality of inspection units includes those that inspect hatching eggs and those that do not (dummies).

As described above, the hatching egg inspection apparatus 1 includes: a plurality of the light emitter 13, the light emitter 13 being disposed two dimensionally at prescribed positions; the light receiver 18, which are provided in a one-to-one relationship to the light emitter 13 and each of which receives light from its corresponding light emitter 13; and an egg container T, which is for arraying a hatching egg between each of the light emitter 13 and its corresponding light receiver 18; furthermore, each hatching egg E is inspected by the corresponding light receiver 18 receiving, of the light from the corresponding light emitter 13, the transmitted light that transmitted through the interior of the corresponding hatching egg. In the hatching egg inspection apparatus 1, among the plurality of light emitter 13, when the one light emitter 18 is emitting light, the other light emitter 18 within the prescribed range centered on the one light emitter 13 do not emit light.

According to the hatching egg inspection apparatus 1, the plurality of light emitter 13 is disposed two dimensionally, namely, in a first direction and a second direction that intersects the first direction. These light emitter 13 are provided in correspondence with the plurality of hatching eggs E, which is arrayed for inspection. The light from each light emitter transmits through the corresponding hatching egg E and is received by the corresponding light receiver 18. The light that transmits through the hatching egg E possesses information about the embryo inside the hatching egg, and the hatching egg can be inspected by analyzing the light received by the light receiver 18.

In the hatching egg inspection apparatus 1, the light emitter 13 are disposed two dimensionally, and consequently numerous hatching eggs E arrayed two dimensionally in the egg container T are inspected all together. Thereby, numerous hatching eggs can be inspected in a short period of time. Furthermore, among the plurality of light emitter 13 disposed two dimensionally, when one light emitter 13 is emitting light, the other light emitter 13 within the prescribed range do not emit light. Thereby, the light receiver 18 corresponding to the one light emitter 13 is not affected by the emission of light by the other light emitter 13 and consequently can receive only the light of the corresponding one light emitter 13. Accordingly, the hatching eggs E can be inspected accurately.

In addition, each light receiver may receive the transmitted light, which is time varying, pertinent to biological information about the interior of the hatching egg.

The biological information includes the heart rate, the fetal movement, and the like of the embryo inside the hatching egg, and consequently the transmitted light received by each light receiver 18 changes extremely minutely due to the heart rate, the fetal movement, and the like of the embryo. Because the hatching egg inspection apparatus 1 inspects the hatching egg based on these minute changes, the light receiver 18 tends to be affected by noise. However, according to the hatching egg inspection apparatus 1, the one light receiver 18 does not receive the lights from the other light emitter 13 within the prescribed range centered on the one light emitter 13 corresponding to the one light receiver 18 and consequently can perform an accurate inspection also based on the minutely changing light.

In the hatching egg inspection apparatus according to the present embodiment, the luminous energy of each light emitter 13 is adjusted such that the inspection can be performed with the corresponding light receiver 18 receiving the optimal luminous energy. Accordingly, the light receiver 18 are adapted to the optimal luminous energy and are set to a high light receiving sensitivity. In this case, if the one light receiver 18 receives light from other non-corresponding light emitter 13, then the inspection accuracy markedly worsens. Accordingly, the one light receiver 18 does not receive the lights from the other light emitter 13 within the prescribed range centered on the one light emitter 13 corresponding to the one light receiver 18, and thereby accurate inspection can be performed.

In addition, in the hatching egg inspection apparatus according to the present embodiment, the luminous energy of each light emitter 13 is adjusted, and thereby there are cases in which other light emitter adjacent to the one light emitter emits light particularly strongly. In such a case, too, the other light emitter within the prescribed range, namely, the light emitter adjacent to the one light emitter, do not emit light simultaneous with the one light emitter, and consequently the hatching eggs E can be inspected accurately.

The hatching egg inspection apparatus 1 is used in the hatching egg inspecting method according to the embodiment of the present invention. This inspecting method includes: when the one light emitter 13 of the plurality of light emitter 13 is receiving light, the other light emitter 13 within the prescribed range centered on the one light emitter 13 do not emit light; the corresponding light receiver 18 receives the transmitted light, of the lights from all the light emitter 13, that passed through the interior of the hatching egg E; and the hatching egg E is inspected based on the light received by the light receiver 18.

According to the present inspecting method, the plurality of light emitter 13 of the inspection apparatus are disposed two dimensionally, namely, in the first direction and the second direction, which intersects the first direction. These light emitter 13 are provided in correspondence with the plurality of hatching eggs arrayed two dimensionally in the egg container T for performing the inspection. The light from each light emitter 13 transmits through the corresponding hatching egg E and is received by the corresponding light receiver 18. The light that transmits through the hatching egg E possesses information related to the biological activity of the embryo inside the hatching egg, and the hatching egg can be inspected by analyzing the light received by the light receiver 18.

In the hatching egg inspecting method according to the embodiment of the present invention, the numerous hatching eggs arrayed two dimensionally are inspected all at once. Thereby, the numerous hatching eggs can be inspected in a short period of time. Furthermore, when the one light emitter of the plurality of light emitter disposed two dimensionally is emitting light, the other light emitter within the prescribed range do not emit light. Thereby, the light receiver corresponding to the one light emitter is not affected by the emission of light of the other light emitter and can receive the light of the corresponding one light emitter. Accordingly, the hatching eggs can be accurately inspected.

<Vibration Isolating Structure>

Next, vibration isolating structures provided to the hatching egg inspection apparatus will be explained. Referencing FIG. 2 once again, the transfer part 20 is fixed to the floor surface, and the transfer part 20 is provided with: a transferring device 21, which transfers the hatching eggs E based on the measurement results supplied by the measuring device 11; and an inviable egg eliminating unit 25, which removes, to the outside of the hatching egg inspection apparatus 1, inviable eggs B that were transferred from the egg container T by the transferring device 21.

A plurality of suction parts 22, which are for selectively vacuum chucking the hatching eggs E, are mounted to the transferring device 21 such that the suction parts 22 correspond to the arrangement of half of the hatching eggs E housed in the egg container T, which is conveyed by a conveying device 31 that is described below. In the present embodiment, a first transfer operation performed by the transferring device 21 transfers half of the plurality of hatching eggs E housed in the egg container T, and a second transfer operation removes the inviable eggs B on the egg container T. A configuration may be adopted such that the suction parts 22 mounted to the transferring device 21 number the same as the caps 14 mounted to the measuring device 11, and the transferring device 21 can remove all the inviable eggs B housed in one egg container T in one transfer operation.

In the transferring device 21, the suction parts 22 can vacuum chuck selectively, based on the determination results of the determination calculating units 46, only those hatching eggs E, among the hatching eggs E on the egg container T, that were determined to be inviable eggs B. As a technique for selectively transferring only the inviable eggs B from the egg container T, it is possible to use, for example, the detailed transfer technique performed by the transfer apparatus recited in Japanese Unexamined Patent Application Publication No. 2012-231700 and the like.

The transferring device 21 is connected via the extending and contracting part 24 to a sliding part 23, which is fixed to the transfer part 20. The sliding part 23 is a conventionally well-known slider that horizontally moves the transferring device 21 from above the egg container T to above the inviable egg eliminating unit 25. When the inviable eggs B are to be transferred, the extending and contracting part 24 lowers the transferring device 21 and brings the suction parts 22 into tight contact with the upper end parts of the inviable eggs B. In addition, after the inviable eggs B have been vacuum chucked, the transferring device 21 is raised to a prescribed position.

The inviable egg eliminating unit 25 is mounted in the transfer part 20 slightly tilted such that the inviable egg eliminating unit 25 can remove, to outside the hatching egg inspection apparatus 1, the inviable eggs B that were transferred from the egg container T by the transferring device 21. When the transferring device 21 releases the vacuum chucking of the inviable eggs B above the inviable egg eliminating unit 25, the inviable eggs B roll along a tilted surface on the inviable egg eliminating unit 25 and are recovered in an inviable egg collection container (not shown), which is placed outside of the hatching egg inspection apparatus 1.

As shown in FIG. 1 and FIG. 2, the inspecting part 10 and the transfer part 20 are disposed spaced apart by a prescribed spacing without making direct contact and are connected via vibration isolating parts 5, which are for isolating or reducing vibration that arises owing to the transfer operation performed by the transferring device 21. Furthermore, the vibration that arises owing to the operation of the transferring device 21 can be isolated via the vibration isolating parts 5 as well as by separating the inspecting part 10 and the transfer part 20.

In addition, the measuring device 11, which is mounted in the inspecting part 10, and the transferring device 21, which is mounted in the transfer part 20, are separated. "Separated" indicates a non-contact state; however, as in the present embodiment, even though the inspecting part 10 and the transfer part 20, wherein the measuring device 11 and the transferring device 21 are mounted, are connected via the vibration isolating parts 5, this aspect is also included in the state in which the measuring device 11 and the transferring device 21 are separated.

To accurately transfer specific inviable eggs B from the egg container T based on the measurement results of the measuring device 11, it is necessary to position the measuring device 11 and the transferring device 21. Connecting the inspecting part 10 and the transfer part 20 via the vibration isolating parts 5 makes it possible to accurately position the measuring device 11 and the transferring device 21 when, for example, the hatching egg inspection apparatus 1 is being installed.

The vibration isolating parts 5 are vibration isolating apparatuses for isolating or reducing the vibration from the extending and contracting part 24, the sliding part 23, and the like that arises in order to drive the transferring device 21. In the present embodiment, rubber vibration isolators are used for the vibration isolating parts 5, but the vibration isolating parts 5 are not limited to rubber vibration isolators as long as the vibration from the extending and contracting part 24, the sliding part 23, and the like that arises when the transferring device 21 is operated can be isolated or reduced; for example, vibration from the extending and contracting part 24, the sliding part 23, and the like may be isolated or reduced by a coil spring, an air spring, and the like.

Figure 10:
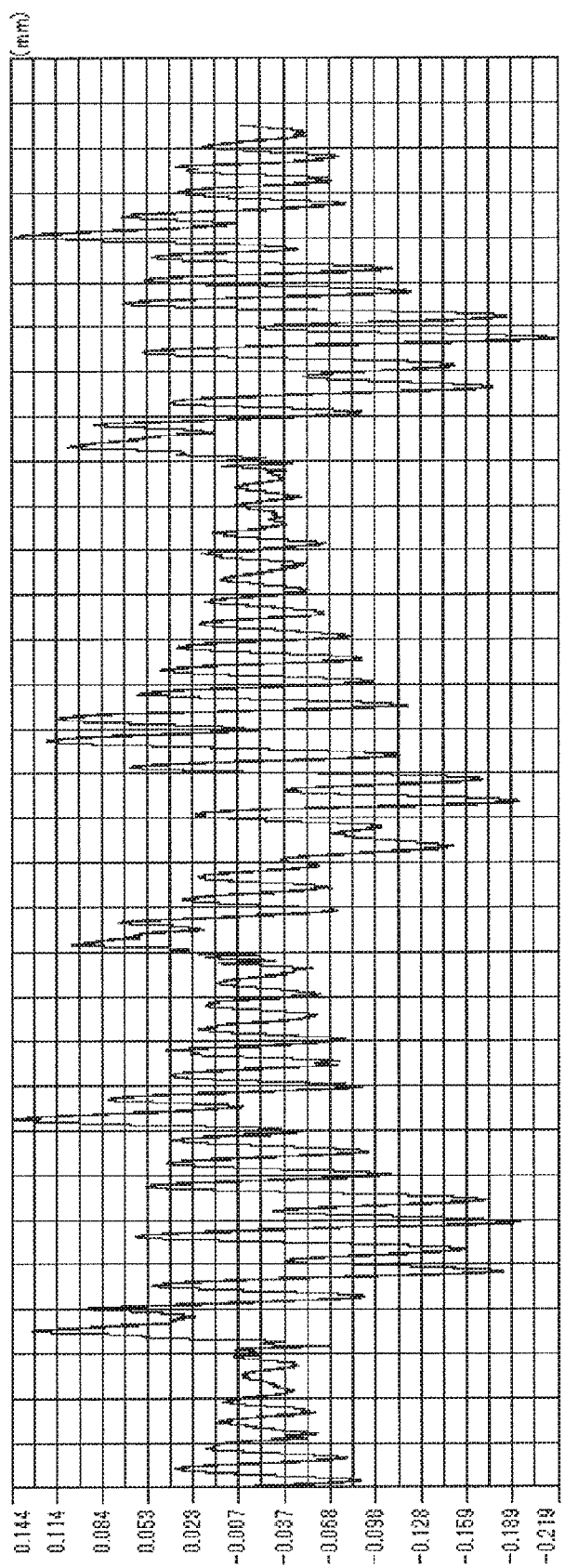
FIG. 10 is a waveform chart that shows the vibration that is transmitted to the inspecting part when a conventional hatching egg inspection apparatus eliminates inviable eggs.

Incidentally, FIG. 10 is a graph that shows the results of using a laser displacement gauge to measure, when the transfer part provided to a conventional hatching egg inspection apparatus is removing inviable eggs, the vibration transmitted to a measuring device connected to the transfer part. The scale of the abscissa is in 40 μs increments, and the scale of the ordinate is in 0.015 mm increments. As shown in the graph, if the transfer part and the measuring device are connected, then the operation of the transfer part generates minute vibrations, which are adversely transmitted to the cap of the measuring device.

If even a small amount of vibration is transmitted to the caps 14 when the transferring device 21 is operating, then the caps 14 vibrate, which causes slight changes also in the light that transmits through the egg owing to the shaking of the egg—even if the egg is a developmentally stopped egg, which increases the probability that the egg will be mistakenly determined to be a viable egg. In the hatching egg inspection apparatus 1, which includes the caps 14 of the measuring device 11 according to the present embodiment, adopting a configuration such that vibration is not transmitted to the caps 14 when the transferring device 21 operates is extremely effective from the standpoint of preventing mistaken determinations.

In addition, the conveying parts 30 are fixed to the floor surface and are provided with a conveying device 31, which is for conveying in a carry-in direction 3, the egg container T wherein the hatching eggs E are housed and for conveying, in a carry-out direction 4, the egg container T after measurement and the like have been performed. The conveying device 31 is a conveyor that sandwiches each egg container T with dogs 32, from the front and rear, in the conveying direction and conveys the egg container T. Both ends of each dog 32 are linked to two chains (not shown), and the egg container T is conveyed, while sliding on a carrying surface 33, by simultaneously driving the two chains.

Although the transfer part 20 and the conveying parts 30 are connected via the vibration isolating parts 5, which are for isolating or reducing vibration that arises due to the transfer operation of the transferring device 21, the transfer part 20 and the conveying part 30 are separated and do not make contact with one another. When, for example, the hatching egg inspection apparatus 1 is being installed, the transfer part 20 and the conveying parts 30 make contact via the vibration isolating parts 5, which makes it possible to accurately position the transferring device 21 and the conveying device 31 when, for example, the hatching egg inspection apparatus 1 is being installed. Furthermore, vibration isolating parts the same as the vibration isolating parts 5 that connect the inspecting part 10 and the transfer part 20 discussed earlier can be used as the vibration isolating parts 5 that connect the transfer part 20 and the conveying parts 30.

Figure 11:
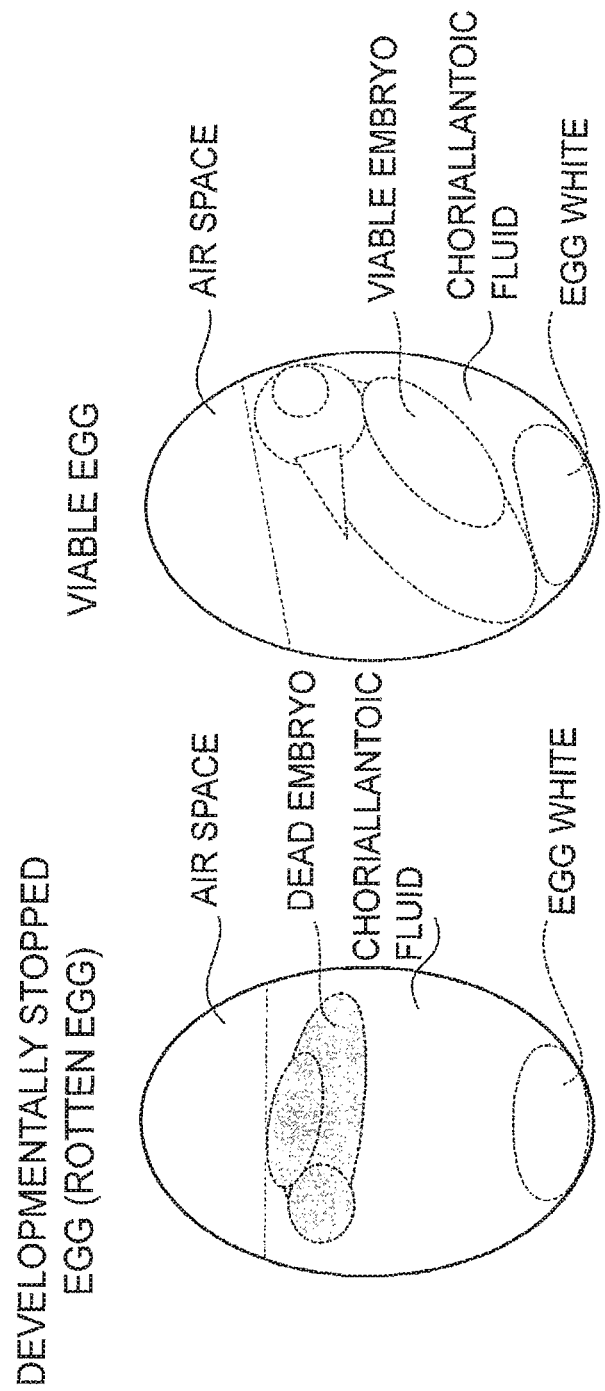
FIG. 11 is a state diagram that shows the internal state of a developmentally stopped egg (a rotten egg) and a viable egg.

Incidentally, because a dead embryo inside a developmentally stopped egg (rotten egg) in the state shown in FIG. 11 is floating in a chorioallantoic fluid, if even a little vibration is transmitted when the transferring device 21 is operating, then the dead embryo will shake from side to side. Such shaking will approximate the motility, the heart rate, and the like of the embryo, and the egg, even though it is a developmentally stopped egg, may be mistakenly determined to be a viable egg. Adopting a configuration such that vibration is not transmitted, when the transferring device 21 is operating, to the conveying device 31 that conveys the hatching eggs E, including developmentally stopped eggs in the state shown in FIG. 11, is extremely effective from the standpoint of preventing mistaken determinations.

As described above, the hatching egg inspection apparatus according to the embodiment of the present invention includes: a measuring device, which measures the vital signs of a plurality of hatching eggs, the hatching eggs being arrayed at prescribed positions; an inspecting part, whereto the measuring device is mounted; a transferring device that, after the measurement performed by the measuring device, transfers, based on the measurement results, prescribed hatching eggs among the plurality of hatching eggs; and a transfer part, whereto the transferring device is mounted; furthermore, when the transferring device is operating in order to transfer the prescribed hatching eggs among the plurality of hatching eggs, the measuring device measures the vital signs of another plurality of hatching eggs; in addition, the inspecting part and the transfer part are disposed spaced apart by a prescribed spacing and the transferring device is separated from the measuring device.

In addition, the hatching egg inspection apparatus further includes: a conveying device, which conveys the plurality of hatching eggs from the position of the measuring device to the position of the transfer part; and conveying parts, whereto the conveying device is mounted; in addition, the conveying parts and the transfer part may be disposed spaced apart by a prescribed spacing and the transferring device may be separated from the conveying device.

In addition, the transfer part includes vibration isolating parts, which isolate or reduce vibration that arises due to the transfer of the hatching eggs by the transferring device; in addition, the transfer part may be connected with the inspecting part and the conveying parts via the vibration isolating parts.

<Operation of Hatching Egg Inspection Apparatus>

Figure 12:
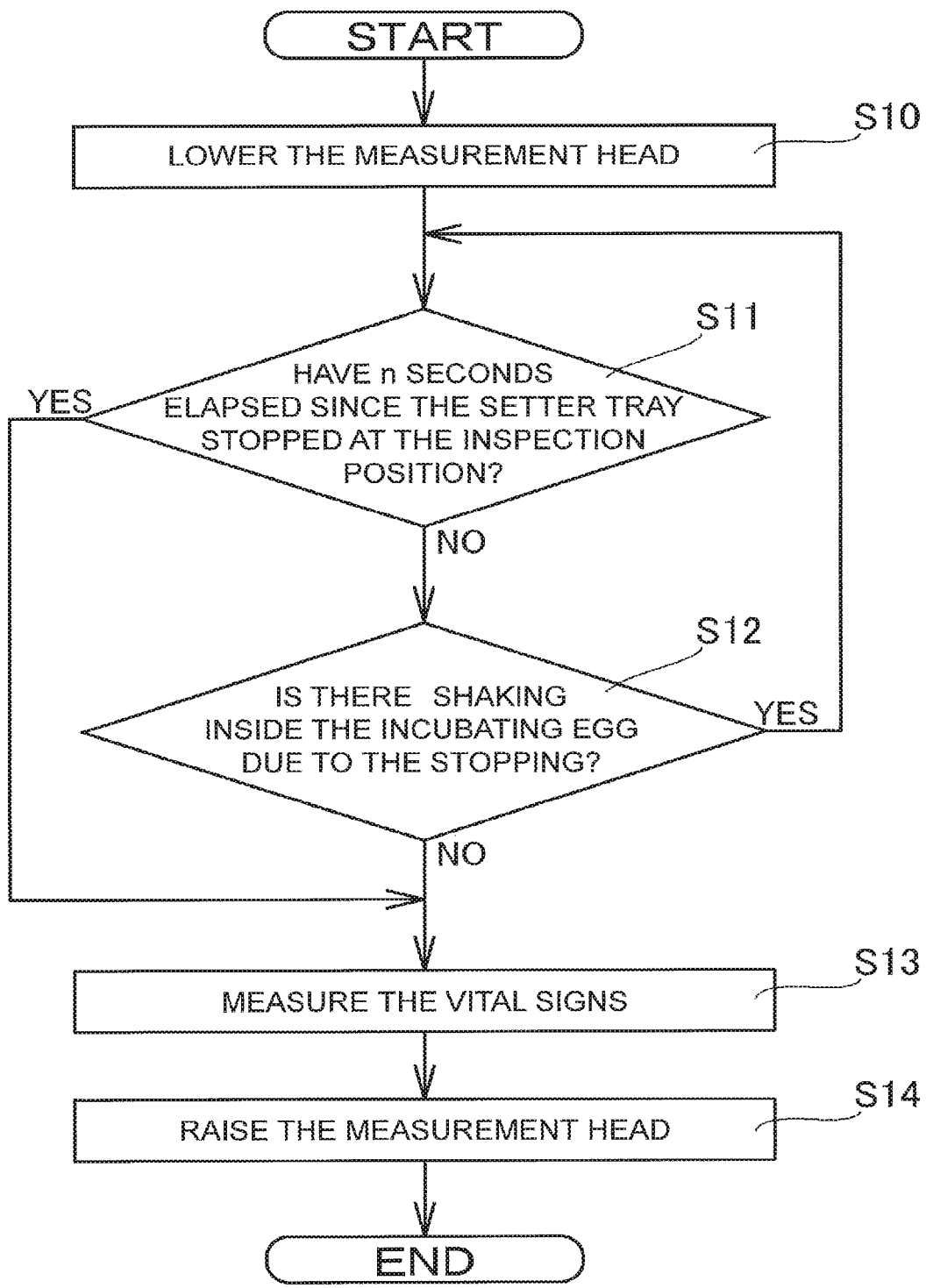
FIG. 12 is a flow chart for explaining the operation of the hatching egg inspection apparatus in the present embodiment.

Next, the operation of the hatching egg inspection apparatus 1 according to the present embodiment will be explained, referencing the flow chart shown in FIG. 12.

The egg container T is conveyed by the conveying device 31 to a position directly below the measuring device 11 (the inspection position). When the egg container T stops at the inspection position, the measuring device 11 brings the caps 14 into close contact with the upper end parts of the hatching eggs E stopped at the inspection position by lowering a measurement head 15 (S10).

Subsequently, after a standby time of n seconds or greater has elapsed since the egg container T stopped at the inspection position (S11), or after it has been confirmed that there is no shaking arising inside the hatching eggs E due to the stopping of the egg container T at the inspection position (S12), a measurement of vital signs is performed (S13).

Thereby, after shaking that arises inside the hatching eggs E has attenuated, it can be determined, based on the vital signs, whether each hatching egg is good or bad. Furthermore, "there is no shaking inside the hatching egg E" includes the case wherein there is shaking to some extent that does not cause a mistaken determination when the measurement of vital signs is performed, and is not limited to the case wherein shaking has been completely eliminated.

If vital signs are measured when a sufficient amount of time has not yet elapsed since the egg container T stopped at the inspection position, then, in the case of the state wherein a dead embryo tends to shake, as inside the developmentally stopped egg (rotten egg) shown in FIG. 11, the dead embryo will shake from side to side owing to inertial force generated when the egg container T was conveyed to the inspection position. Because of such shaking, an inviable egg may adversely be mistakenly determined to be a viable egg even though it is a developmentally stopped egg.

Furthermore, in the present embodiment, the standby time is set to 2 seconds, which is the time within which shaking inside a rotten egg that arises due to inertial force generated when the egg container T has been conveyed at a maximum velocity of 50 cm/s is virtually eliminated, and therefore a mistaken determination does not occur. If the conveying speed of the egg container T is slow, then the standby time may be set short. In addition, the standby time does not need to be always fixed and may be set to n seconds, the value of n modified being as appropriate in accordance with the conveying speed and the like.

In addition, to determine whether there is shaking inside one of the hatching eggs E (in this case, a rotten egg), it is necessary to lower the measurement head 15 and to measure the time varying components of the light that transmits through the hatching egg E as soon as the cap 14 contacts the upper end part of the hatching egg E. The measurement of the time varying components of the light performed at this time is not the measurement of vital signs performed in order to determine whether the hatching egg E is good or bad, but rather the measurement that is performed in order to determine whether there is shaking inside the hatching egg E. Below, the measurement that is performed to determine whether there is shaking inside the hatching egg E is called a "shake measurement."

When the shake measurement is performed, in the case wherein a dead embryo tends to shake, as in the interior of the developmentally stopped egg (rotten egg) shown in FIG. 11, the side to side shaking of the dead embryo owing to the inertial force generated when the egg container T has been conveyed to the inspection position is measured. Such shaking often has a waveform that is clearly different from the waveform of a viable egg, as in the waveform of the developmentally stopped egg (rotten egg) shown in FIG. 13.

Figure 13:
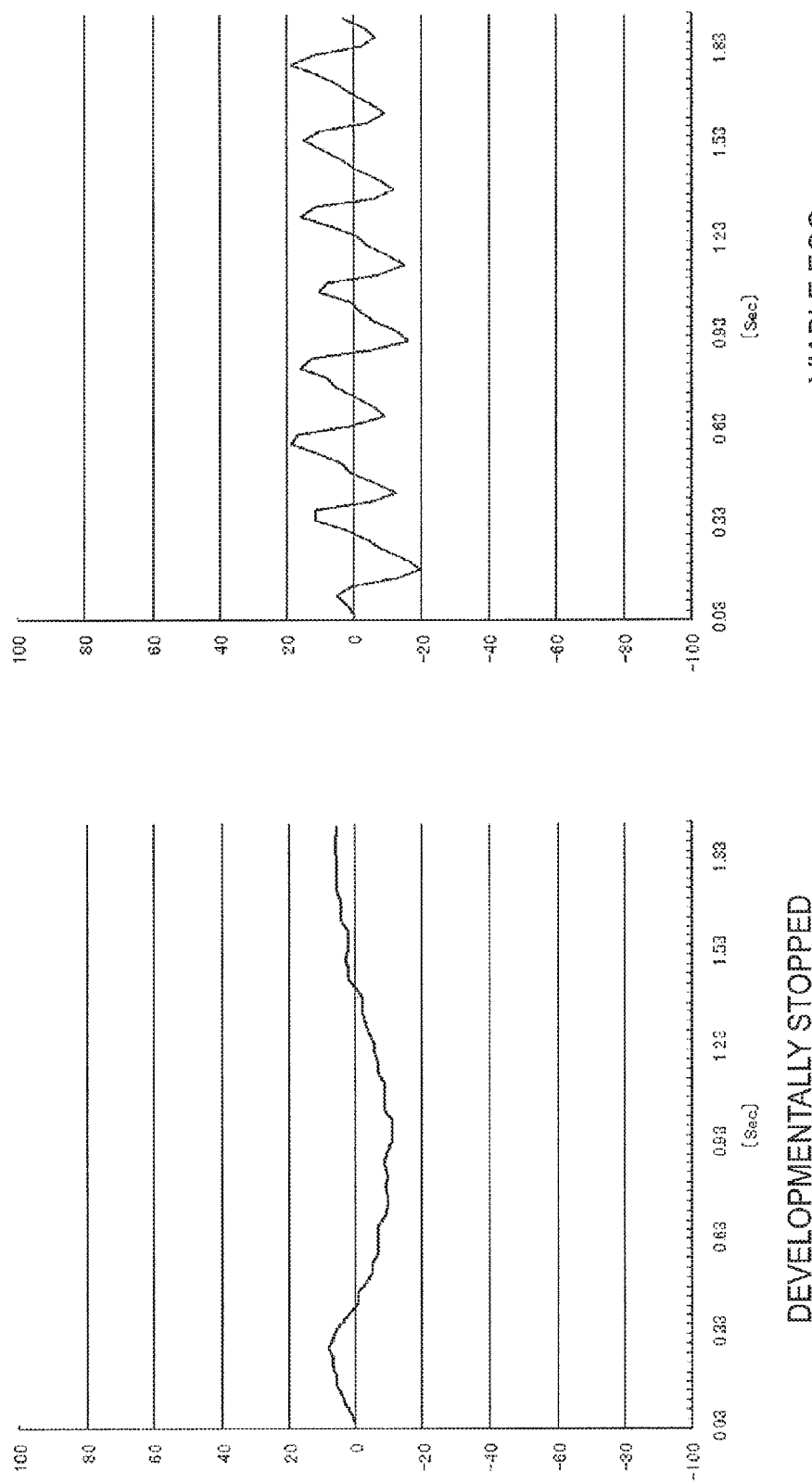
FIG. 13 includes waveform charts that show the time varying components of lights that transmit through a developmentally stopped egg (a rotten egg) and a viable egg.

Here, the details of the graphs of the time varying components of the lights that transmit through the developmentally stopped egg (rotten egg) and the viable egg shown in FIG. 13 will be explained. FIG. 13 includes a graph (left side) of the time varying components of the light that transmitted through the interior of one developmentally stopped egg (rotten egg) of the plurality of hatching eggs E housed in the same egg container T and whose light time varying components were measured simultaneously, and a graph (right side) of the time varying components of the light that transmitted through the interior of one viable egg of the plurality of hatching eggs E housed in the same egg container T and whose light time varying components were measured simultaneously.

In both graphs, the ordinate represents the intensity of the light received by the light receiving device of the measurement head 15, and the abscissa represents time (seconds). The time varying components of the light that transmitted through the interior of the viable egg on the right side include the heart rate, which changes periodically; however, the time varying components of the light that transmitted through the interior of the developmentally stopped egg (rotten egg) on the left side do not include time varying components such as a heart rate but do include the time varying components due to the shaking that arises owing to the inertial force generated when the egg container T has been conveyed.

When shaking is measured by the shake measurement, the vital signs are basically not measured. However, at this point in time, if the fixed time (n seconds) since the egg container T stopped at the inspection position has elapsed (S11), then the vital signs measurement is performed; however, if the fixed time has not elapsed, then the time varying components of the light are measured once again and it is determined whether there is shaking in the interior of the hatching egg E (S12). Furthermore, in the present measurement operation, the "shake measurement" and the "vital signs measurement" are separate; however, instead of separating these, just a one-time measurement of the time varying components of the light may be performed at first and, if a waveform that appears to be shaking is not included therein, then the initially performed measurement of the light time varying components may serve as the vital signs measurement.

When the vital signs measurement is performed, the lights received by the light receiver 18 are converted to electrical signals and sent to the determination calculating units 46. The determination calculating units 46 determine the activity of the hatching eggs based on the electrical signals sent from the inspecting part 10. Subsequently, the measurement head 15 is raised and the hatching eggs E and the caps 14 separate (S14).

When the inspection by the inspecting part 10 is complete, the conveying parts 30 resume conveying and convey the egg container T to the transfer part 20. Based on the inspection result, the transfer part 20 transfers, to the inviable egg eliminating unit 25, those hatching eggs E determined to be inviable eggs. The inviable eggs B on the inviable egg eliminating unit 25 roll down an inclination and are recovered in the collection container for inviable eggs, which is prepared outside of the hatching egg inspection apparatus 1.

In the hatching egg inspection apparatus according to the present embodiment, egg containers are sequentially conveyed to one inspection position and sequentially inspected. However, a configuration may be adopted wherein two of the inspection positions are provided and inspections are performed alternately at the inspection positions. Namely, a configuration may be adopted wherein, when the hatching eggs for one inspection unit housed in the egg container at one inspection position are being inspected, the hatching eggs of another one inspection unit in the other inspection apparatus is being conveyed.

Thereby, while the hatching eggs of the one inspection unit at one of the inspection positions is being inspected, the hatching eggs of the other one inspection unit of the other inspection position is being conveyed, and the attenuation of shaking during that conveying is awaited. A configuration may be adopted wherein, subsequently, when the inspection of the hatching eggs of the one inspection unit has ended, the measuring part is moved to the other inspection position and the hatching eggs of the other one inspection unit, wherein the shaking during transport has attenuated, is inspected.

As described above, the hatching egg inspection apparatus includes: a measuring device, which measures the vital signs of a plurality of hatching eggs that have been stopped at a measurement position; and determination calculating units, which determine whether the hatching eggs are good or bad based on the vital signs measured by the measuring device; in addition, the determination calculating units determine whether the hatching eggs are good or bad based on the vital signs after the plurality of incubating eggs has stopped at the inspection position and the shaking that arises inside the hatching eggs due to the stopping has attenuated.

The hatching egg inspection apparatus may further include the conveying part that conveys the plurality of hatching eggs to the inspection position. The determination calculating units may determine whether the hatching eggs are good or bad based on the vital signs after n seconds have elapsed since the plurality of hatching eggs has stopped at the measurement location. The abovementioned n seconds is modified, as appropriate, by the inspection unit.

The determination calculating units may determine whether the hatching eggs are good or bad based on the vital signs after the plurality of hatching eggs has stopped at the inspection position and there is no longer any shaking arising inside the hatching eggs due to the stopping.

The inspecting part may have inspection positions in at least two locations, and, when the measuring part is measuring the vital signs of the plurality of hatching eggs that has been stopped at one of the inspection positions, the plurality of hatching eggs at the other inspection position may be stopped or moved.

The hatching egg inspecting method includes: a step of stopping the plurality of hatching eggs at the inspection position; a step of measuring the vital signs of the plurality of hatching eggs that have been stopped at the inspection position; and a of determining whether the hatching eggs are good or bad based on the vital signs after the plurality of hatching eggs has stopped at the inspection position and the shaking that arises inside the hatching eggs due to the stopping has attenuated.

According to the hatching egg inspection apparatus and the hatching egg inspecting method according to the present embodiment, the measurement of vital signs is performed after the shaking that arises internally owing to the transporting of the hatching eggs housed in the egg container to the inspection, and therefore there is no mistaken determination wherein, for example, a rotten egg whose dead embryo inside is shaking or an inviable egg such as an unfertilized egg wherein the yolk inside is shaking is determined to be a viable egg.

<Measurement Data Process>

Figure 14:
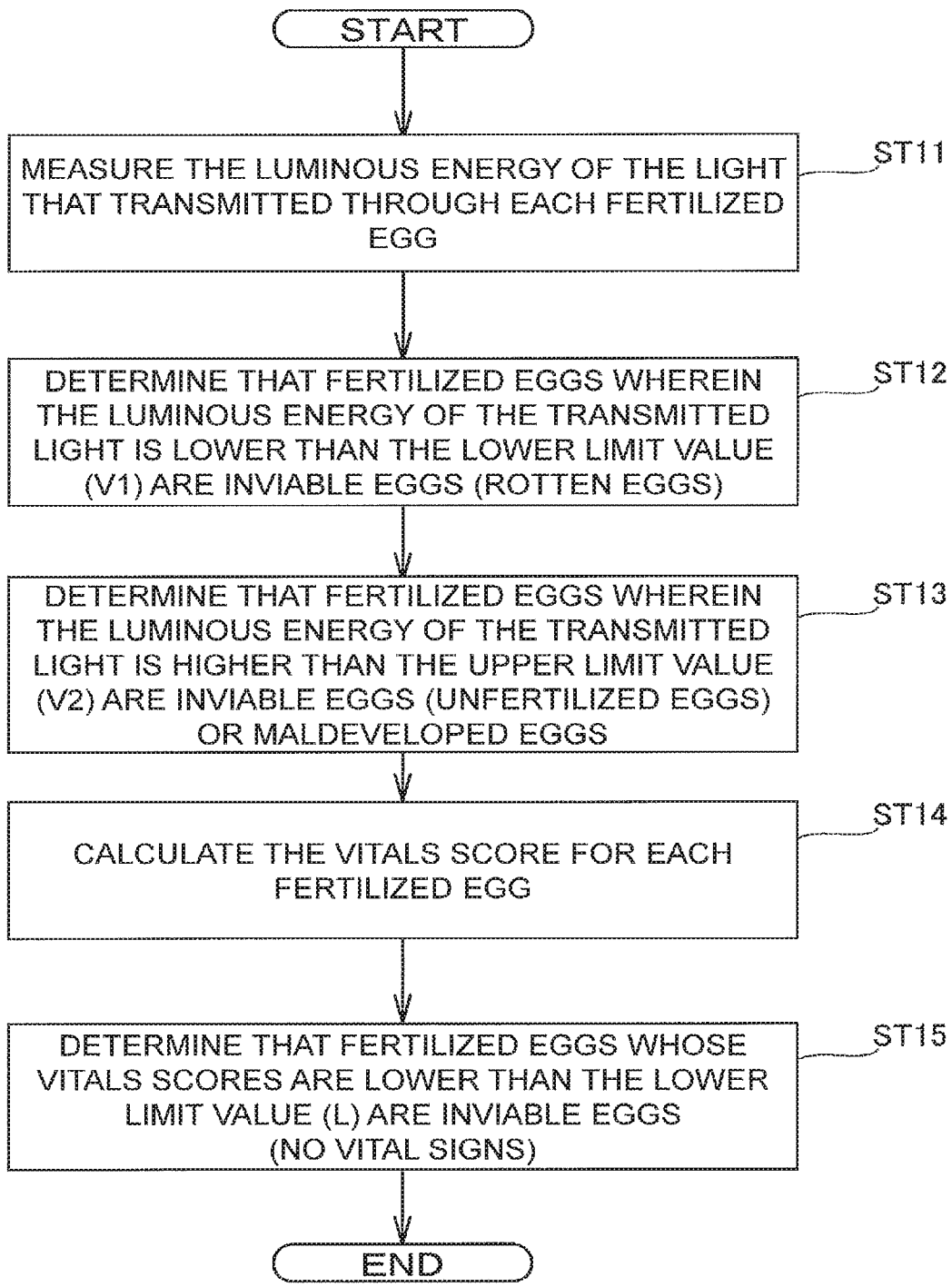
FIG. 14 is a flow chart that shows the flow of a threshold process of a determination calculating unit.

Furthermore, the flow of a measurement data process, which is performed by the determination calculation, will be explained referencing the flow chart shown in FIG. 14.

The lights received by the light receiver are converted to electrical signals and sent to the determination calculating units 46. In the determination calculating units 46, first, the luminous energy of the light that transmitted through each hatching egg E is measured (ST11).

Figure 15:
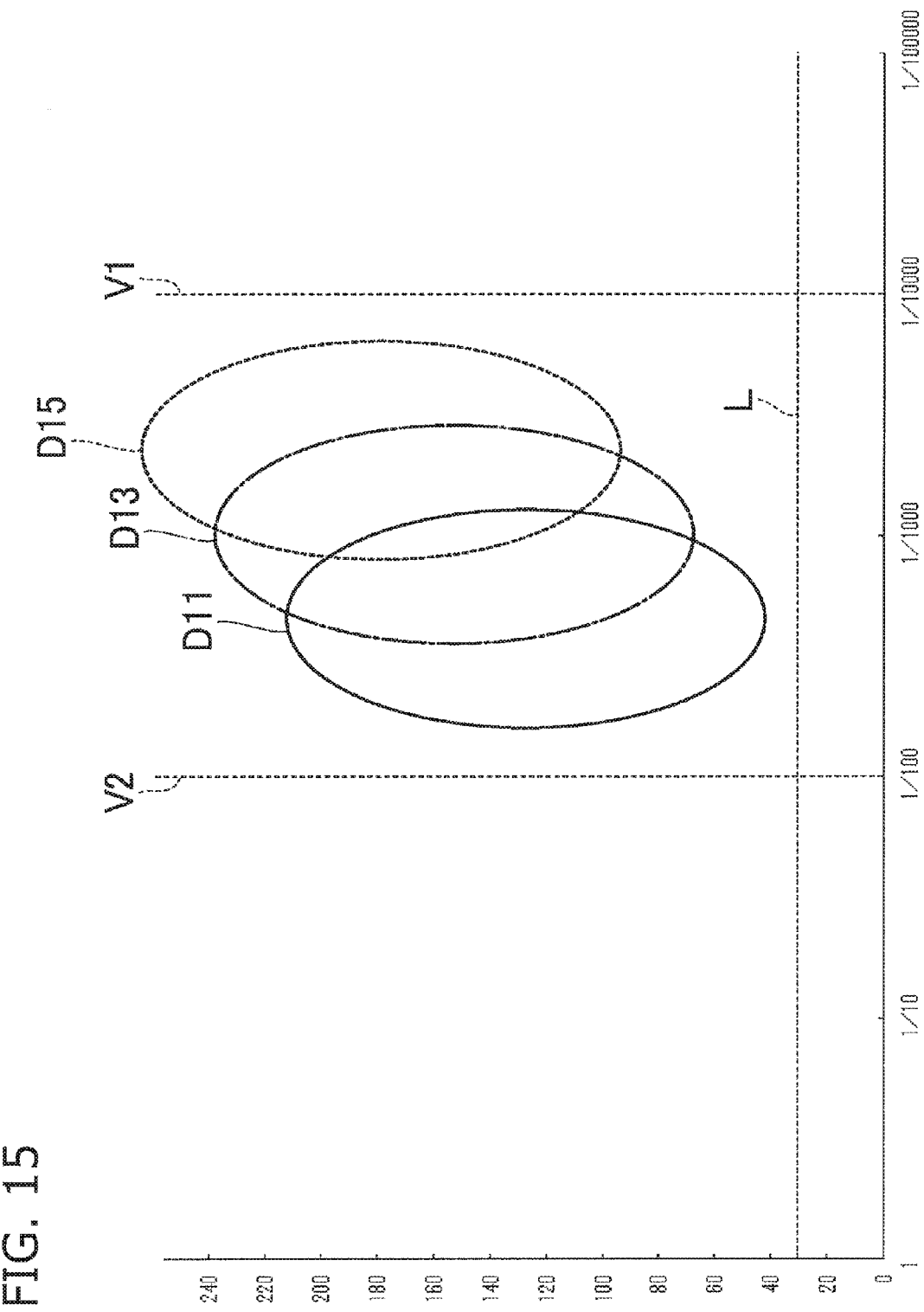
FIG. 15 is a semilogarithmic graph that shows a lower limit value V1 and an upper limit value V2 of transmitted luminous energy, and a lower limit value L that serves as a prescribed value of a vitals score.

FIG. 15 is a semilogarithmic graph wherein the ordinate represents a vitals score and the abscissa represents the transmitted luminous energy. The maximum value of the transmitted luminous energy is 1; furthermore, in the semilogarithmic graph of FIG. 15, the higher the transmitted luminous energy, the further left the value, and the lower the transmitted luminous energy, the further right the value.

In the present embodiment, as shown in FIG. 15, the transmitted luminous energy has a lower limit value V1, which serves as a prescribed value, at the location of $\frac{1}{10000}$; furthermore, hatching eggs in the area (the right side of V1) wherein the transmitted luminous energy is lower than the lower limit value V1 that serves as the prescribed value are rotten eggs, wherein the internal embryos and the like have rotted, and are consequently determined to be inviable eggs F (ST12).

Furthermore, the flow of the present process provides an upper limit value V2, which serves as another prescribed value, at the location of $\frac{1}{100}$, the transmitted luminous energy of which is higher than that of the lower limit value V1 that serves as the prescribed value; furthermore, incubating eggs in the area (the left side of V2) wherein the transmitted luminous energy is higher than the upper limit value V2 that serves as a prescribed value are determined to be inviable eggs F (unfertilized eggs) or maldeveloped eggs (ST13). A maldeveloped egg is an incubating egg wherein, although the embryo is not dead, the development of the embryo is late and, depending on the hatchery, is eliminated from the incubating process simultaneously with the inviable eggs; consequently, in the flow of the present process, it is subject to being eliminated by the transfer part 20, the same as the inviable eggs F are.

When the transmitted luminous energy of each hatching egg E is measured and it is determined, based on the transmitted luminous energy, that the egg is an inviable egg F or a maldeveloped egg, next, the vitals score for each hatching egg E is calculated (ST14). In the present embodiment, a lower limit value L, which serves as a prescribed value, is provided at the location where the vitals score is 30 points; an incubating egg whose vitals score is in an area (lower side of L) lower than the lower limit value L that serves as a prescribed value is either an unfertilized egg or has developed only to a certain extent; however, because it is a developmentally stopped egg whose embryo inside has died for some reason, it is determined to be an inviable egg F (no vital signs) (ST15), whereupon the processing of the determination calculating unit 46 ends.

On the left side of the upper limit value V2, too, which serves as a prescribed value, if there is an egg whose vitals score exceeds 30 points, which would be a hatching egg E that should be determined to be a viable egg owing to changes in the electrical signal, it is determined to be a maldeveloped egg as discussed earlier. Providing the upper limit value V2 that serves as a prescribed value of the transmitted luminous energy makes it possible to discover such maldeveloped eggs and remove them as needed.

Here, the relationship between the incubation day count and the transmitted luminous energy and vitals score will be explained. An area D11 indicated by a solid line in FIG. 15 describes the central area for the case wherein a hatching egg group was measured on the 11th day of incubation and the measurement results of those hatching eggs were plotted. Similarly, an area D13 indicated by a chain line and an area D15 indicated by a broken line describe central areas for the cases in which hatching egg groups were measured on the 13th and 15th days of incubation, respectively, and the measurement results of those incubating eggs were plotted.

Because there is a correlation between the incubation day count and the transmitted luminous energy and vitals score, the upper limit value V2, which serves as a prescribed value of the transmitted luminous energy, may be changed in accordance with the incubation day count of the incubating egg, which is the measurement target, for example, $1/100$ for an incubating egg on the 11th day of incubation, $1/250$ for an incubating egg on the 13th day of incubation, and $1/700$ for an incubating egg on the 15th day of incubation. Changing the upper limit value V2 in accordance with the incubation day count in this manner makes it possible to perform the determination more accurately. In addition, by likewise changing the lower limit value L, too, which serves as the prescribed value of the vitals score, in accordance with the incubation day count, it is possible to perform determinations more accurately.

In addition, in the present specification, the flow of the process of the determination calculating units 46 is described using a semilogarithmic graph as in FIG. 15 for the purpose of explanation; however, in actuality, arithmetic processing units of the determination calculating units perform determinations without creating such a semilogarithmic graph. Furthermore, a variety of modifications can be effected in the flow of the process of the determination calculating units 46 explained so far; furthermore, the vitals score calculating method, the method of determining viable eggs and inviable eggs, the upper and lower limit values that serve as prescribed values, and the like are merely illustrative examples and the present invention is not limited thereto.

As described above, the hatching egg inspection apparatus converts the lights that pass through the interiors of hatching eggs into electrical signals and, based on changes in these electrical signals, namely, based on vital signs, determines whether the hatching eggs are viable eggs or inviable eggs. If the transmitted luminous energy of an incubating egg that should be determined to be a viable egg based on changes in the electrical signal is lower than a first prescribed value, then the hatching egg is determined to be an inviable egg.

The hatching egg inspection apparatus has a second prescribed value, which is higher than the first prescribed value; furthermore, if the transmitted luminous energy of a hatching egg that should be determined to be a viable egg based on changes in the electrical signal is higher than the second prescribed value, then the hatching egg may be determined to be an inviable egg. In addition, if the transmitted luminous energy of an incubating egg that should be determined to be a viable egg based on changes in the electrical signal is higher than the second prescribed value, then the hatching egg may be determined to be a maldeveloped egg. In addition, a hatching egg may be determined to be a viable egg based on only one of either the first prescribed value or the second prescribed value. Furthermore, the incubation day count of the hatching egg to be inspected may be 15 days or fewer.

The above explained an exemplary case wherein the target was an egg, but the egg includes various eggs such as chicken eggs, duck eggs, quail eggs, and the like.

The embodiments disclosed herein are merely exemplary, and the present invention is not limited thereto. The present invention is described by the scope of the claims rather than the scope explained above and is intended to include all modifications within the scope of the claims and within equivalent meanings and scopes.

INDUSTRIAL APPLICABILITY

The present invention can provide, in a hatching egg inspection apparatus that uses vital signs, an inspection apparatus that has high inspection accuracy.

What is claimed is:

1. A hatching egg inspection apparatus for inspecting hatching eggs arrayed at predetermined positions, comprising:
    a measuring device configured to measure vital signs of hatching eggs arrayed at the predetermined positions and produce a measured result;
    an inspecting part whereto the measuring device is mounted;
    a transferring device configured to transfer a predetermined hatching egg among the hatching eggs arrayed at the predetermined positions based on the measured result after the measurement by the measuring device;
    a transfer part comprising the transferring device, wherein when the transferring device transfers the predetermined hatching egg among the hatching eggs, the measuring device measures vital signs of other hatching eggs,
    the inspecting part and the transfer part are disposed spaced apart by a predetermined spacing so as to reduce vibration from the transferring device to the measuring device thereby preventing vibration of the hatching eggs, and
    comprising a first vibration isolating part configured to isolate or reduce vibration generated that arises when the transferring device transfers the predetermined hatching egg, wherein
    the inspecting part and the transfer part are connected with each other via the first vibration isolating part.

2. The hatching egg inspection apparatus according to claim 1, further comprising:
    a conveying device configured to transport a hatching egg from a position of the measuring device to a position of the transfer part; and
    a conveying part to which the conveying device is attached, wherein
    the conveying part and the transfer part are arranged separate from each other, and the transferring device is separated from the conveying device.

3. The hatching egg inspection apparatus according to claim 2, further comprising a second vibration isolating part configured to isolate or reduce vibration that arises when the transferring device transfers the predetermined hatching egg, wherein
    the transfer part and the conveying part are connected with each other via the second vibration isolating part.

4. The hatching egg inspection apparatus according to claim 3, wherein when the transferring device transfers a plurality of predetermined hatching eggs among the first plurality of hatching eggs, the measuring device measures vital signs of the second plurality of hatching eggs.

5. A hatching egg inspection apparatus for inspecting hatching eggs arrayed at predetermined positions, comprising:
    a measuring device configured to measure vital signs of hatching eggs arrayed at the predetermined positions and produce a measured result;
    an inspecting part whereto the measuring device is mounted;
    a transferring device configured to transfer a predetermined hatching egg among the hatching eggs arrayed at the predetermined positions based on the measured result after the measurement by the measuring device;
    a transfer part comprising the transferring device, wherein when the transferring device transfers the predetermined hatching egg among the hatching eggs, the measuring device measures vital signs of other hatching eggs,
    the inspecting part and the transfer part are disposed spaced apart by a predetermined spacing so as to reduce vibration from the transferring device to the measuring device thereby preventing vibration of the hatching eggs, and further comprising:

a conveying device configured to transport a hatching egg from a position of the measuring device to a position of the transfer part; and a conveying part to which the conveying device is attached, wherein the conveying part and the transfer part are arranged separate from each other, and the transferring device is separated from the conveying device, further comprising a vibration isolating part configured to isolate or reduce vibration that arises when the transferring device transfers the predetermined hatching egg, wherein the transfer part and the conveying part are connected with each other via the vibration isolating part.

6. The hatching egg inspection apparatus according to claim 5, wherein when the transferring device transfers a plurality of predetermined hatching eggs among the first plurality of hatching eggs, the measuring device measures vital signs of the second plurality of hatching eggs.

7. The hatching egg inspection apparatus according to claim 1, wherein when the transferring device transfers a plurality of predetermined hatching eggs among the first plurality of hatching eggs, the measuring device measures vital signs of the second plurality of hatching eggs.

* * * * *